United States Patent
Morino et al.

(10) Patent No.: US 11,158,034 B2
(45) Date of Patent: Oct. 26, 2021

(54) IMAGE INSPECTION DEVICE, IMAGE INSPECTION METHOD, AND IMAGE INSPECTION DEVICE COMPONENT

(71) Applicant: QD LASER, INC., Kawasaki (JP)

(72) Inventors: Seiji Morino, Kawasaki (JP); Makoto Suzuki, Kawasaki (JP); Manabu Ishimoto, Kobe (JP)

(73) Assignee: QD LASER, INC., Kawasaki (JP)

( * ) Notice: Subject to any disclaimer, the term of this patent is extended or adjusted under 35 U.S.C. 154(b) by 142 days.

(21) Appl. No.: 16/318,263

(22) PCT Filed: Aug. 7, 2017

(86) PCT No.: PCT/JP2017/028558
§ 371 (c)(1),
(2) Date: Jan. 16, 2019

(87) PCT Pub. No.: WO2018/034181
PCT Pub. Date: Feb. 22, 2018

(65) Prior Publication Data
US 2020/0342582 A1 Oct. 29, 2020

(30) Foreign Application Priority Data
Aug. 18, 2016 (JP) .............................. JP2016-160857

(51) Int. Cl.
*G06T 7/00* (2017.01)
*G02B 27/01* (2006.01)
(Continued)

(52) U.S. Cl.
CPC ........ *G06T 7/0002* (2013.01); *G02B 27/0172* (2013.01); *G06T 3/00* (2013.01);
(Continued)

(58) Field of Classification Search
CPC ........... G06T 7/0002; G06T 7/97; G06T 3/00; G06T 7/60; G06T 2207/30168; G02B 27/0172; H04N 9/3194
See application file for complete search history.

(56) References Cited

U.S. PATENT DOCUMENTS 5,889,625 A 3/1999 Chen
6,661,470 B1 12/2003 Kawakami
(Continued)

FOREIGN PATENT DOCUMENTS

CN 1253652 A 5/2000
CN 1601370 A 3/2005
(Continued)

OTHER PUBLICATIONS

Office Action of Chinese Patent Application No. 201780050293.6 dated Apr. 21, 2020 (11 sheets, 13 sheets translation, 24 sheets total).
(Continued)

*Primary Examiner* — Michael Robert Cammarata
(74) *Attorney, Agent, or Firm* — Kratz, Quintos & Hanson, LLP

(57) ABSTRACT

An image inspection device includes a mounting unit on which an image projection device that directly projects an image on a retina of a user is to be mounted; a condensing lens that condenses a light beam emitted from the image projection device mounted on the mounting unit; a detector on which an inspection image is projected and detected; and a controller that inspects the inspection image detected by the detector. The image inspection device inspects the image projected by the image projection device, which directly projects the image on the retina of the user.

4 Claims, 32 Drawing Sheets

(51) Int. Cl.
  *G06T 3/00* (2006.01)
  *G06T 7/60* (2017.01)
  *H04N 9/31* (2006.01)

(52) U.S. Cl.
  CPC ............... *G06T 7/60* (2013.01); *G06T 7/97* (2017.01); *H04N 9/3194* (2013.01); *G02B 2027/014* (2013.01); *G06T 2207/30168* (2013.01)

(56) References Cited

U.S. PATENT DOCUMENTS

| | | | |
|---|---|---|---|
| 9,979,956 B1* | 5/2018 | D'Amico | G06T 7/11 |
| 2005/0024585 A1 | 2/2005 | Dai | |
| 2005/0068500 A1 | 3/2005 | Tamura | |
| 2005/0213846 A1* | 9/2005 | Matsuda | H04N 5/74 382/275 |
| 2006/0018550 A1* | 1/2006 | Rash | G06T 7/0002 382/218 |
| 2006/0232665 A1 | 10/2006 | Schowengerdt | |
| 2010/0182423 A1* | 7/2010 | Kawasue | G01B 11/24 348/130 |
| 2010/0214418 A1 | 8/2010 | Germain | |
| 2012/0002167 A1 | 1/2012 | Kondoh | |
| 2013/0135463 A1* | 5/2013 | Aratani | G06K 9/3216 348/135 |
| 2013/0258486 A1* | 10/2013 | Ionescu | G02B 27/0172 359/630 |
| 2015/0138451 A1* | 5/2015 | Amitai | G02B 27/0081 349/11 |
| 2016/0103324 A1 | 4/2016 | Arakawa | |
| 2019/0137857 A1* | 5/2019 | Sugawara | H04N 9/3188 |
| 2020/0342582 A1* | 10/2020 | Morino | G02B 27/02 |

FOREIGN PATENT DOCUMENTS

| | | |
|---|---|---|
| CN | 1691744 A | 11/2005 |
| CN | 101991404 A | 3/2011 |
| CN | 103458772 A | 12/2013 |
| JP | 2003-279446 A | 10/2003 |
| JP | 2007-523674 A | 8/2007 |
| JP | 2009-156992 A | 7/2009 |
| JP | 2010-522347 A | 7/2010 |
| JP | 2012-011146 A | 1/2012 |
| JP | 2015-111231 A | 6/2015 |
| WO | 2004/112567 A2 | 12/2004 |
| WO | 2004/112576 A2 | 12/2004 |
| WO | 2008/149712 A1 | 12/2008 |
| WO | 2014/128657 A1 | 8/2014 |

OTHER PUBLICATIONS

International Search Report for International Application No. PCTJP2017/028558 dated Oct. 24, 2017 (2 Sheets).
Partial Supplementary European Search Report for European Patent Application No. 17841406.6 dated Jul. 26, 2019 (13 pages).
Supplementary European Search Report for corresponding European Patent Application No. 17841406.6 dated Nov. 19, 2019 (11 sheets).
Office Action of counterpart Chinese Patent Application No. 2018-534351: Notification of Reasons for Refusal dated Feb. 9, 2021 (5 sheets, 5 sheets translation, 10 sheets total).
Office Action of corresponding Chinese Application No. 201780050293.6 dated Nov. 6, 2020 (8 sheets, 12 sheets translation, 20 sheets total).
Office Action of corresponding Chinese Patent Application No. 201780050293.6 dated Mar. 12, 2021 (7 sheets, 10 sheets translation, 17 sheets total).

* cited by examiner

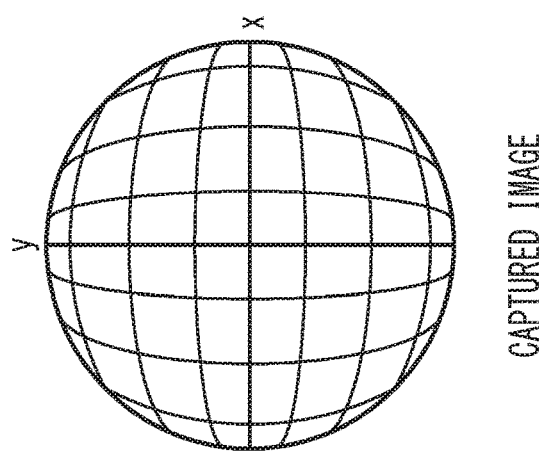
FIG. 8C TRANSFORMED IMAGE
FIG. 8B CAPTURED IMAGE
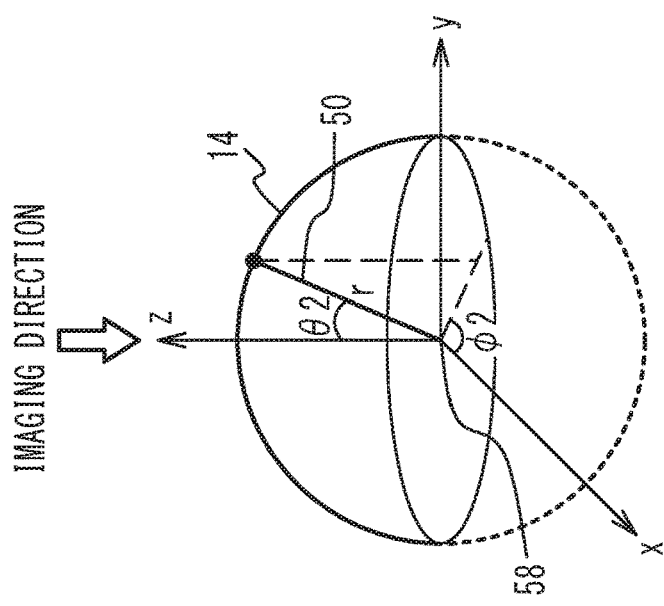
FIG. 8A

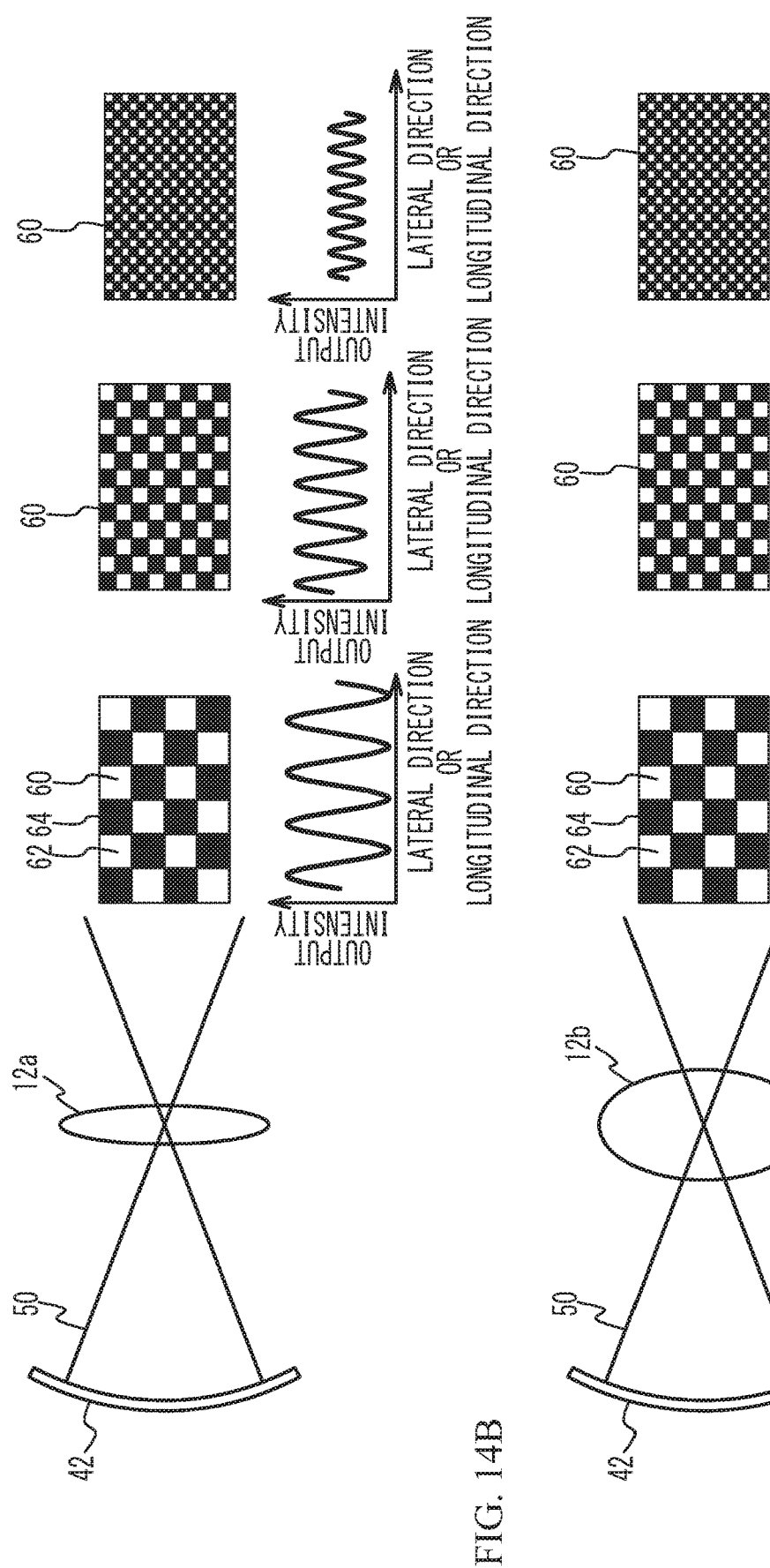

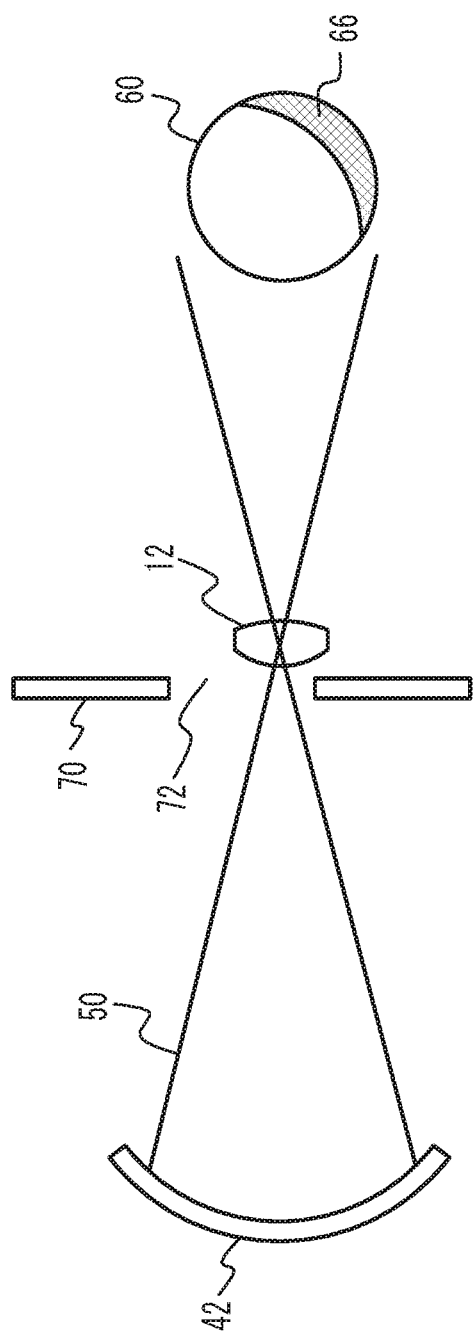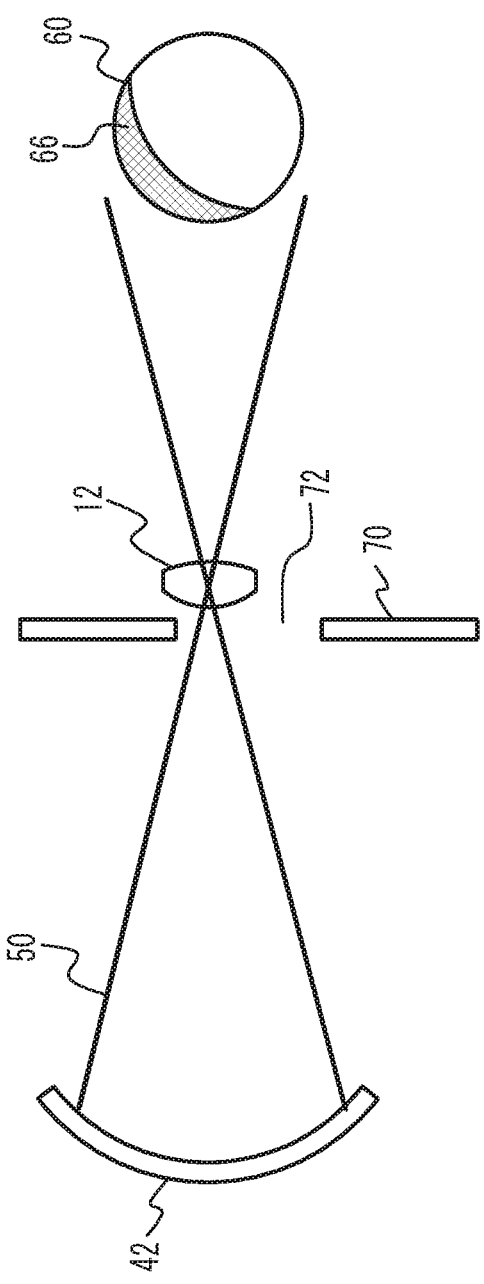
FIG. 23A
FIG. 23B

IMAGE INSPECTION DEVICE, IMAGE INSPECTION METHOD, AND IMAGE INSPECTION DEVICE COMPONENT

TECHNICAL FIELD

The present invention relates to an image inspection device, an image inspection method, and an image inspection device component.

BACKGROUND ART

There have been known image projection devices, such as head-mounted displays (HMDs), that directly project an image on the retina of the user by using a light beam emitted from a light source (for example, Patent Document 1). In such image projection devices, the method referred to as Maxwellian view is used. In Maxwellian view, a scanning light formed of a light beam forming the image is converged near the pupil, and the image (a retina image) is then projected on the retina. There have been also known distortion inspection devices that measure the distortion amount of an inspection object (for example, Patent Document 2).

PRIOR ART DOCUMENTS

Patent Document

Patent Document 1: Japanese Patent Application Publication No. 2015-111231
Patent Document 2: International Publication No. 2008/149712

SUMMARY OF THE INVENTION

Problem to be Solved by the Invention

A method of inspecting an image by the user actually wearing an image projection device and viewing a projected image is considered as a method of inspecting an image projected on a retina in the image projection device that directly projects an image onto the retina of the user. However, in this method, since persons other than the user wearing the image projection device are unable to view the image, the judgement varies depending on the user, and the judgement criteria is thus vague.

The present invention has been made in view of the above problems, and aims to inspect an image projected by an image projection device that directly projects an image on the retina of the user in a retina scanning laser display.

Means for Solving the Problem

The present invention is an image inspection device including: a mounting unit on which an image projection device that directly projects an image on a retina of a user is to be mounted; a condensing lens configured to condense a light beam emitted from the image projection device mounted on the mounting unit; and a target projection unit on which an inspection image is to be projected by irradiation with the light beam condensed by the condensing lens; and an inspection unit configured to inspect the inspection image projected on the target projection unit.

In the above configuration, an imaging unit configured to capture the inspection image projected on the target projection unit in a shape of a substantial hemisphere having an opening at the condensing lens side; and an image transformation unit configured to transform the inspection image captured by the imaging unit from a polar coordinate system expressed by a moving radius from a center point of the substantial hemisphere and an angle into a Cartesian coordinate system may be provided, and the inspection unit may be configured to inspect the inspection image that has been transformed by the image transformation unit.

In the above configuration, the target projection unit may be configured to allow the inspection image to pass therethrough, and the imaging unit may be configured to capture the inspection image that has passed through the target projection unit.

In the above configuration, a reflection system located on a light path of the light beam between the condensing lens and the target projection unit may be provided, and the imaging unit may be configured to capture the inspection image that has been reflected by the target projection unit and the reflection system.

In the above configuration, the reflection system may include a polarizer, a polarization beam splitter, and a quarter wavelength plate.

In the above configuration, the target projection unit may have a planar shape.

In the above configuration, the inspection unit may be configured to inspect at least one of distortion, resolution, brightness, a pattern shape, a gamma characteristic, a contrast ratio, an aspect ratio, and a hue of the inspection image.

In the above configuration, the inspection image projected on the target projection unit may include a first inspection image projected by the light beam condensed by the condensing lens having a first focal length and a second inspection image projected by the light beam condensed by the condensing lens having a second focal length different from the first focal length, and the inspection unit may be configured to measure a first resolution of the first inspection image and a second resolution of the second inspection image, and inspect whether a ratio of a difference between the first resolution and the second resolution to a difference between the first focal length and the second focal length is within a predetermined range.

In the above configuration, the inspection image projected on the target projection unit may include a plurality of the first inspection images having different spatial frequencies and a plurality of the second inspection images having different spatial frequencies, and the inspection unit may be configured to calculate a spatial frequency at which a contrast ratio is 0.5 as the first resolution with use of the plurality of the first inspection images, calculate a spatial frequency at which a contrast ratio is 0.5 as the second resolution with use of the plurality of the second inspection images, and inspect whether the ratio of the difference between the first resolution and the second resolution to the difference between the first focal length and the second focal length is within the predetermined range.

In the above configuration, the inspection image projected on the target projection unit may include an inspection pattern having patterns with different brightness, and the inspection unit may be configured to inspect the resolution of the inspection image based on change in brightness of the inspection pattern.

In the above configuration, an apertured plate that has an aperture through which the light beam passes near the condensing lens and is movable in a plane direction perpendicular to an optical axis of the condensing lens may be provided, the inspection image projected on the target projection unit may include a plurality of the inspection images projected on the target projection unit when the aperture is located at different positions as the apertured plate moves, and the inspection unit may be configured to inspect whether a difference in average brightness and/or a difference in pattern shape among the plurality of the inspection images is within a predetermined range.

In the above configuration, a detector that detects an image may be provided, the detector being located in the target projection unit having a planar shape, the target projection unit may be movable in a direction vertical to a plane of the target projection unit, and the inspection unit may be configured to measure a size of a region of convergence of the light beam by identifying a position of the detector and a size of the inspection image at the position as the target projection unit moves.

The present invention is an image inspection method including: a step of projecting an inspection image on a target projection unit by causing a light beam forming the inspection image to be emitted from an image projection device that directly projects an image on a retina of a user, causing the light beam to pass through a condensing lens, and irradiating the target projection unit with the light beam, and a step of inspecting the inspection image projected on the target projection unit.

In the above configuration, a step of capturing the inspection image projected on the target projection unit in a shape of a substantial hemisphere having an opening at the condensing lens side; and a step of transforming the inspection image captured in the step of capturing from a polar coordinate system expressed by a moving radius from a center point of the substantial hemisphere and an angle into a Cartesian coordinate system may be included, and the step of inspecting may include inspecting the inspection image that has been transformed in the step of transforming.

In the above configuration, the target projection unit may have a planar shape.

In the above configuration, the step of inspecting may include inspecting at least one of distortion, resolution, brightness, a pattern shape, a gamma characteristic, a contrast ratio, an aspect ratio, and a hue of the inspection image.

In the above configuration, the step of projecting may include projecting, as the inspection image, a first inspection image formed of the light beam that has passed through the condensing lens with a first focal length and a second inspection image formed of the light beam that has passed through the condensing lens with a second focal length, and the step of inspecting may include measuring a first resolution of the first inspection image and a second resolution of the second inspection image, and inspecting whether a ratio of a difference between the first resolution and the second resolution to a difference between the first focal length and the second focal length is within a predetermined range.

In the above configuration, the step of projecting may include projecting a plurality of the first inspection images having different spatial frequencies and a plurality of the second inspection images having different spatial frequencies, and the step of inspecting may include calculating, as the first resolution, a spatial frequency at which a contrast ratio is 0.5 with use of the plurality of the first inspection images, calculating, as the second resolution, a spatial frequency at which a contrast ratio is 0.5 with use of the plurality of the second inspection images, and inspecting whether the ratio of the difference between the first resolution and the second resolution to the difference between the first focal length and the second focal length is within the predetermined range.

In the above configuration, the step of projecting may include projecting the inspection image including an inspection pattern having patterns with different brightness on the target projection unit, and the step of inspecting may include inspecting the resolution of the inspection image based on change in brightness of the inspection pattern.

In the above configuration, the step of projecting may include projecting a plurality of the inspection images formed of the light beam passing through an aperture located at different positions due to movement of an apertured plate, which has the aperture through which the light beam passes near the condensing lens, in a plane direction perpendicular to an optical axis of the condensing lens, and the step of inspecting may include inspecting whether a difference in average brightness and/or a difference in pattern shape among the plurality of the inspection images is within a predetermined range.

In the above configuration, a step of identifying a position of a detector, which is mounted in the target projection unit and detects an image, and a size of the inspection image detected at the position as the target projection unit moves, the target projection unit having a planar shape and being movable in a direction vertical to a plane of the target projection unit; and a step of measuring a size of a region of convergence of the light beam by an identified position of the detector and an identified size of the inspection image may be included.

The present invention is an image inspection device component used as the above target projection unit, wherein the image inspection device component is composed of a material having a high light-diffusion property and flat wavelength distribution.

In the above configuration, the material may be a mixture of a material transmitting light and quarts and barium sulfate, or a material transmitting light of which a surface is coated with nanodiamond.

Effects of the Invention

The present invention enables to inspect an image projected by an image projection device that directly projects an image on the retina of the user.

BRIEF DESCRIPTION OF THE DRAWINGS

FIG. 8A through FIG. 8C are diagrams for describing curved image transformation;

FIG. 14A and FIG. 14B are diagrams (No. 1) for describing the second example of the inspection method of the resolution of an image;

FIG. 23A and FIG. 23B are diagrams for describing the inspection method of the brightness and the pattern shape of an image;

EMBODIMENTS FOR CARRYING OUT THE INVENTION

Hereinafter, embodiments of the present invention will be described with reference to drawings.

First Embodiment

Figure 1:
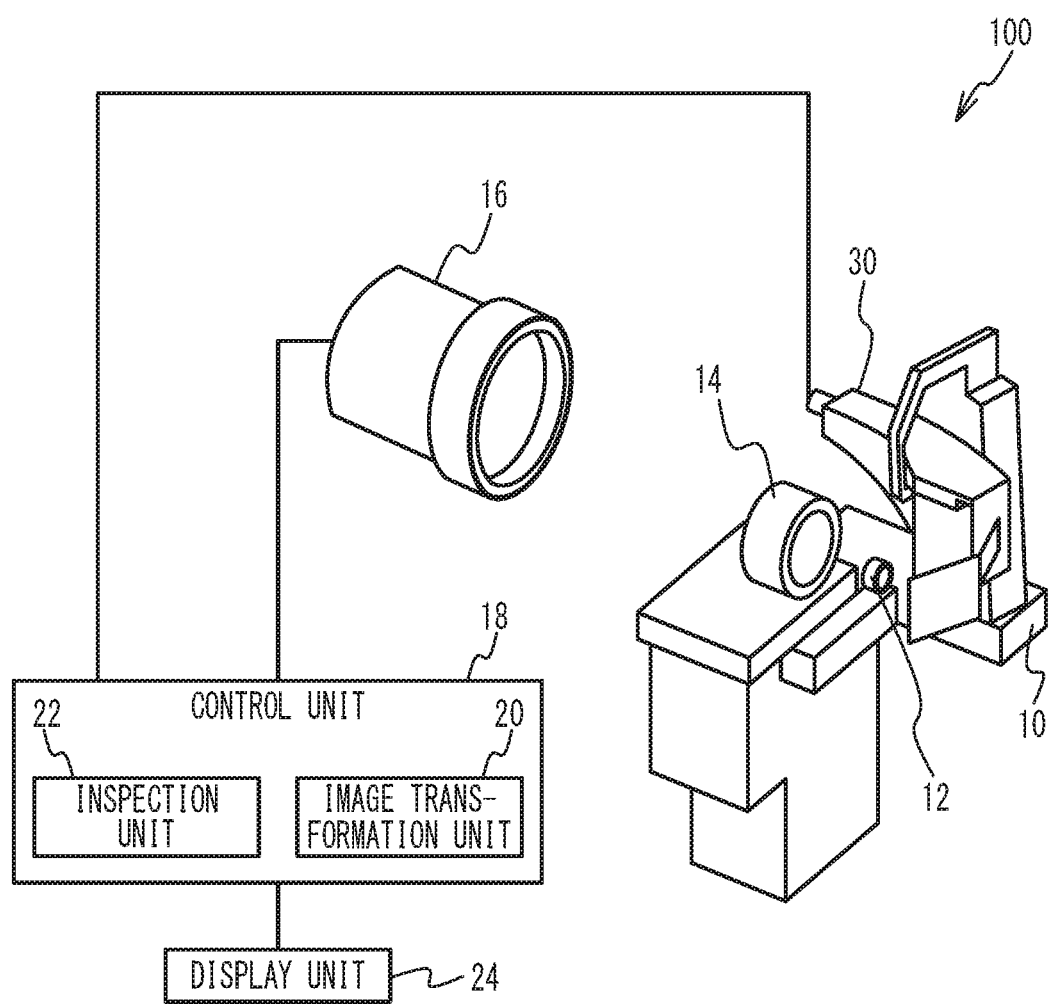
FIG. 1 illustrates an image inspection device in accordance with a first embodiment.

FIG. 1 is a diagram for illustrating an image inspection device 100 in accordance with a first embodiment. As illustrated in FIG. 1, the image inspection device 100 of the first embodiment includes a mounting unit 10, a condensing lens 12, a target projection unit 14, an imaging unit 16, a control unit 18, and a display unit 24.

Figure 2:
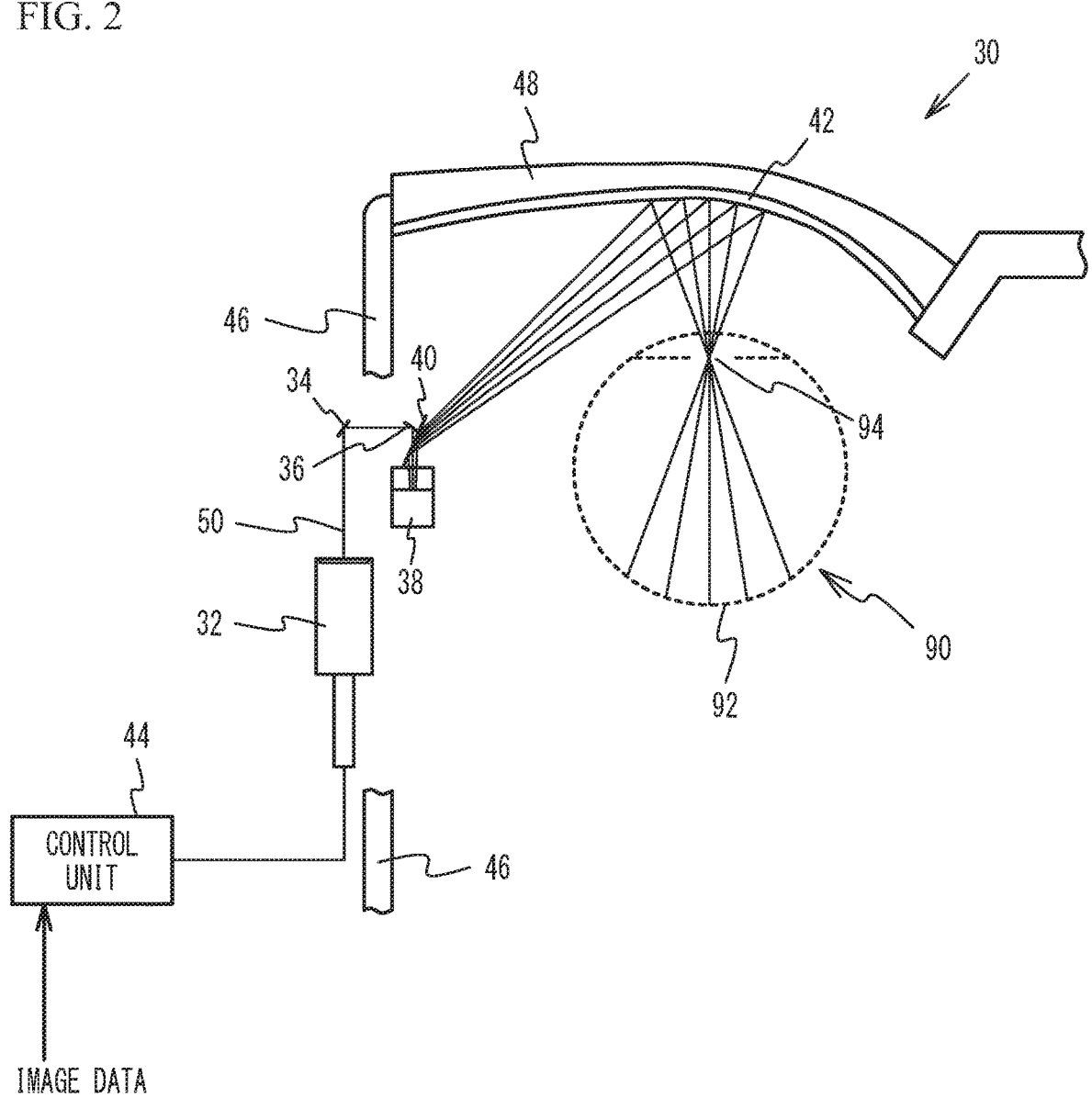
FIG. 2 is a top view of an image projection device.

An image projection device 30, as a test object, that directly projects an image on the retina of the user is mounted on the mounting unit 10. Here, an example of the image projection device 30 is described with use of FIG. 2. FIG. 2 is a top view of the image projection device 30. The image projection device 30 is a retina projection type head-mounted display utilizing Maxwellian view in which the retina of the eyeball of the user is directly irradiated with a light beam that causes the user to view an image.

As illustrated in FIG. 2, the image projection device 30 includes a light source 32, a mirror 34, a mirror 36, a scanning unit 38, a mirror 40, a projection unit 42, and a control unit 44. The light source 32 is arranged in a temple 46 of a spectacle type frame. The light source 32 emits a light beam 50 of, for example, single wavelength or multiple wavelengths under instructions from the control unit 44. The light beam 50 includes a light beam for projecting an image on a retina 92 of an eye ball 90 of the user, and is, for example, visible light of a red laser light (wavelength: approximately 610 nm to 660 nm), a green laser light (wavelength: approximately 515 nm to 540 nm), and a blue laser light (wavelength: 440 nm to 480 nm). Non-limiting examples of the light source 32 emitting red, green, and blue laser lights include a light source in which respective laser diodes for RGB (Red Green Blue), a three-color synthesis device, and a micro collimating lens are integrated.

The scanning unit 38 is arranged in the temple 46 of the spectacle type frame. The scanning unit 38 scans the light beam 50 emitted from the light source 32 in the horizontal direction and the vertical direction. The scanning unit 38 is, for example, a Micro Electro Mechanical System (MEMS) mirror. The light beam 50 emitted from the light source 32 is reflected by the mirror 34 and the mirror 36, and then enters the scanning unit 38.

A scanning light formed of the light beam 50 scanned by the scanning unit 38 is reflected by the mirror 40 toward a lens 48 of the spectacle type frame. The projection unit 42 is arranged on the surface closer to the eye ball 90 of the lens 48. Accordingly, the light beam 50 scanned by the scanning unit 38 enters the projection unit 42. The projection unit 42 is a half mirror having a free curved surface or a half mirror having a composite structure of a free curved surface and a diffraction surface. Thus, the scanning light formed of the light beam 50 that has entered the projection unit 42 converges near a pupil 94 of the eye ball 90 and is then emitted to the retina 92. This allows the user to recognize the image formed of the light beam 50 and visually recognize an external world image through the lens.

The control unit 44 is composed of a processor such as a Central Processing Unit (CPU), and memories such as a Random Access Memory (RAM) and a Read Only Memory (ROM), and the processor operates according to programs stored in the memory, and controls the entire of the image projection device 30 such as controlling the light source 32 to cause the light beam 50 based on input image data to be emitted from the light source 32. The processor and the memory may be provided to the spectacle type frame, or may be provided to an external device such as a mobile terminal.

Figure 3:
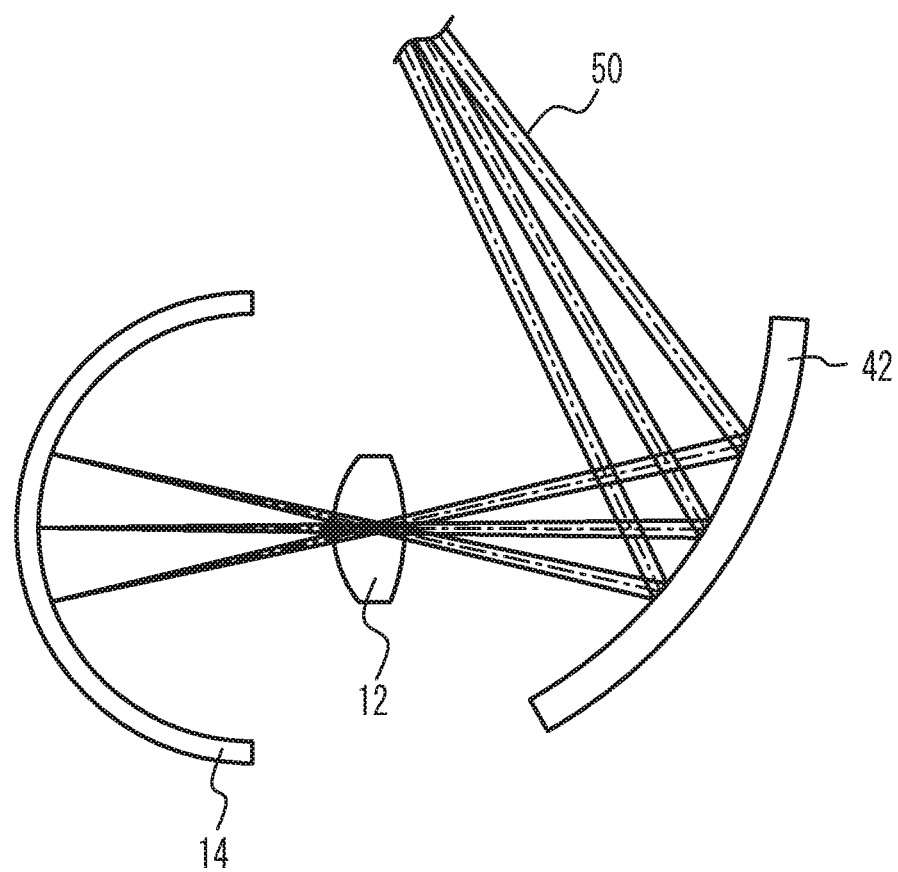
FIG. 3 is a diagram for describing irradiation of a target projection unit with a light beam emitted from the image projection device.

FIG. 3 is a diagram for describing irradiation of the target projection unit 14 with the light beam 50 emitted from the image projection device 30. In FIG. 2, the center portion of the light beam 50 having a limited luminous flux diameter is illustrated, while in FIG. 3, the light beam 50 is illustrated with a limited luminous flux diameter, and its center portion is indicated by a chain line. As illustrated in FIG. 1 and FIG. 3, the condensing lens 12 is located on the optical path through which the light beam 50 reflected by the projection unit 42 passes and at the position at which the scanning light formed of the light beam 50 converges. The condensing lens 12 condenses the light beam 50 that has entered from the projection unit 42.

The target projection unit 14 is located near the condensing spot of the light beam 50 by the condensing lens 12. The target projection unit 14 is formed of glass in the shape of a hemisphere of which the side closer to the condensing lens 12 opens, and having a film translucent to the light beam 50 on the inner surface thereof. The target projection unit 14 may be formed of a material translucent to the light beam 50. When the target projection unit 14 is irradiated with the light beam 50, an image is projected on the target projection unit 14. Since the target projection unit 14 is translucent to the light beam 50, the target projection unit 14 displays the image projected by the light beam 50 and allows the image to pass therethrough.

The above-described structure allows the condensing lens 12 that condenses the light beam 50 to be considered as a crystalline lens of the eye ball, and allows the target projection unit 14 having a surface in the shape of a hemisphere to be considered as the retina of the eye ball. That is, the condensing lens 12 corresponding to the crystalline lens and the target projection unit 14 corresponding to the retina form a pseudo eye (often referred to as a dummy eye or an eye ball screen model, hereinafter, described as the dummy eye). For this reason, the diameter of the target projection unit 14 preferably corresponds to the typical dimension of the eye ball, and is preferably configured to be approximately 23 mm to 25 mm. In addition, when it is assumed that the target projection unit 14 in the shape of a hemisphere is in the shape of a sphere, the scanning light formed of the light beam 50 in the part corresponding to the pupil is preferably configured to be within the range of the general dimension of the pupil (for example, approximately 5 mm to 7 mm) so that this configuration is equivalent to the situation in which the light beam 50 passes through the pupil of the eye ball.

Figure 4A:
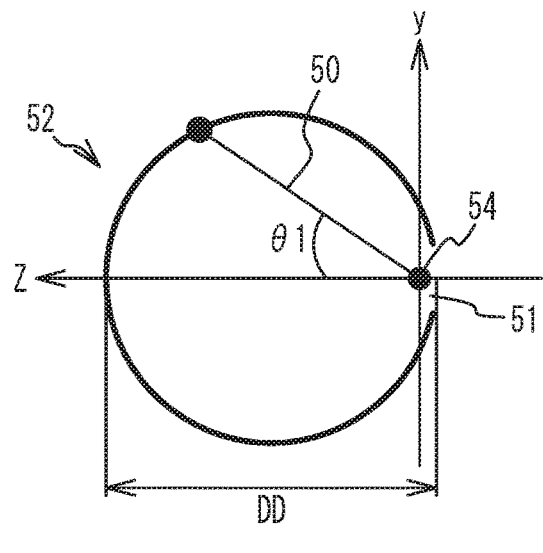
FIG. 4A through FIG. 4D are conceptual drawings of a pseudo eye (a dummy eye)
Figure 4B:
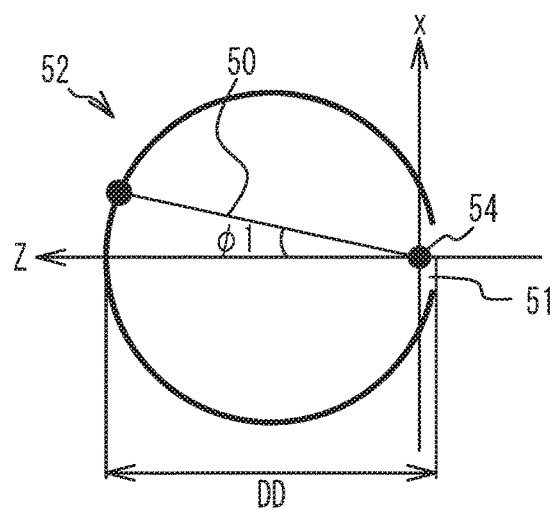
Figure 4C:
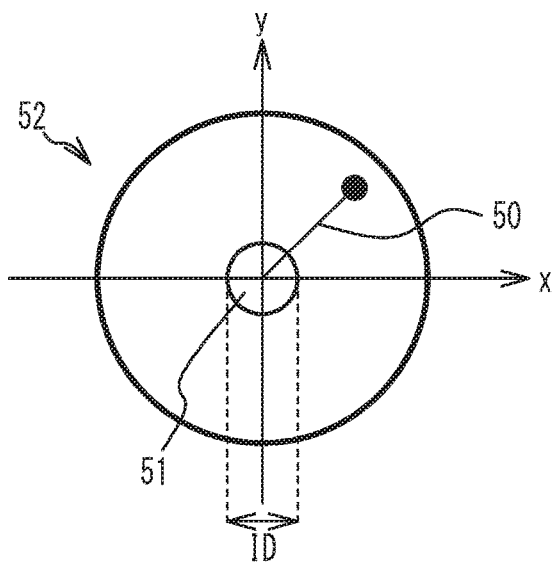
Figure 4D:
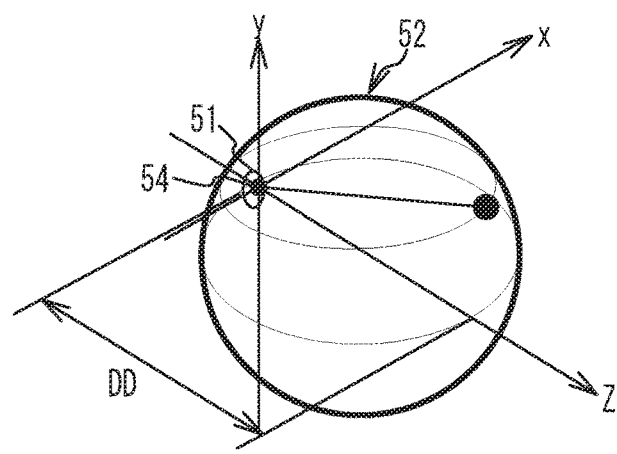
Figure 5:
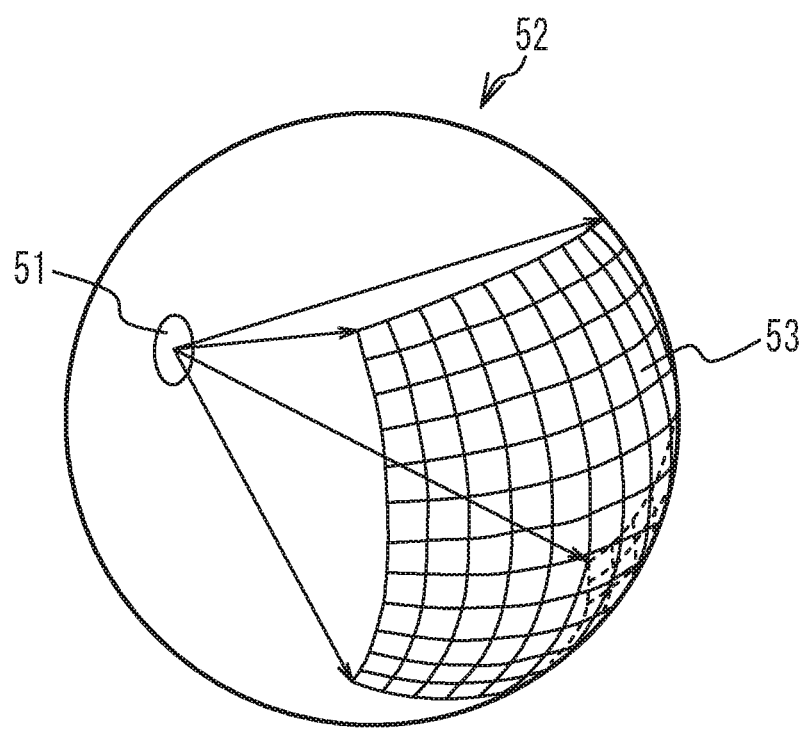
FIG. 5 illustrates an image region to be projected on the pseudo eye (the dummy eye)

FIG. 4A through FIG. 4D are conceptual drawings of a pseudo eye (a dummy eye). FIG. 5 is a diagram illustrating an image region to be projected on the pseudo eye (the dummy eye). FIG. 4A is a side view of a dummy eye 52, FIG. 4B is a top view of the dummy eye 52, FIG. 4C is a front view of the dummy eye 52, and FIG. 4D is a perspective view of the dummy eye 52. As illustrated in FIG. 4A through FIG. 4D, the diameter DD of the dummy eye 52 (i.e., the diameter of the target projection unit 14) is, for example, 24 mm. The light beam 50 enters the dummy eye 52 through a pupil 51 (for example, the aperture having a diameter ID of 7 mm). The light beam 50 enters the dummy eye at an angle $\theta 1$ in the y-axis direction (vertical direction) and at an angle $\varphi 1$ in the x-axis direction (horizontal direction) with respect to the z-axis passing through the center of the dummy eye 52 and a convergence point 54 of the scanning light. Irradiation of the dummy eye 52 with the light beam 50 causes an image to be projected. That is, an image is projected on the target projection unit 14 constituting the dummy eye 52. Since the part corresponding to the retina of the dummy eye 52 has a curved surface shape, an image region 53 projected on the dummy eye 52 is as illustrated in FIG. 5. The material for the target projection unit 14 constituting the dummy eye 52 is preferably a material that is thin, can be processed into a sphere shape, has a high light diffusion property, and has a flat wave length dispersion of the diffused light. Non-limiting examples of the material for the target projection unit 14 include translucent frosted glass, a mixture of glass or acryl, which transmits light, and quartz and $BaSO_4$ (barium sulfate), or glass or acryl of which the surface is coated with nanodiamond that is diamond having a diamond crystal structure and a particle size of nanosize. The above-described dummy eye 52 is useful for measuring, for example, the resolution and/or the distortion of the wide field of view (FOV). Since the optical design such as resolution is optimized on the retina surface, the accurate measurement is preferably performed at the position of the retina when the field of view is wide.

As illustrated in FIG. 1, the imaging unit 16 is located at the opposite side of the target projection unit 14 from the condensing lens 12. The imaging unit 16 captures an image projected on the target projection unit 14 and passing through the target projection unit 14. The imaging unit 16 is, for example, a camera (a CCD camera or a CMOS camera). The imaging unit 16 having resolution higher than the scanning lines of the image to be projected on the target projection unit 14 is used.

The control unit 18 is composed of a processor such as a Central Processing Unit (CPU) and memories such as a Random Access Memory (RAM) and a Read Only Memory (ROM), and the processor operates according to programs stored in the memory, and controls the entire of the image inspection device 100. For example, the control unit 18 inputs inspection image data to the image projection device 30 mounted on the mounting unit 10, and captures an inspection image projected on the target projection unit 14 with the imaging unit 16. The control unit 18 functions as an image transformation unit 20 that transforms the inspection image captured by the imaging unit 16 from a polar coordinate system, which is expressed by the moving radius from the center point of the hemispherical shape of the target projection unit 14 and the angle, into the Cartesian coordinate system, and functions as an inspection unit 22 that inspects the inspection image that is the inspection image captured by the imaging unit 16 and transformed by the image transformation unit 20. The display unit 24 is, for example, a liquid crystal display, and displays the inspection result of the inspection image.

Figure 6:
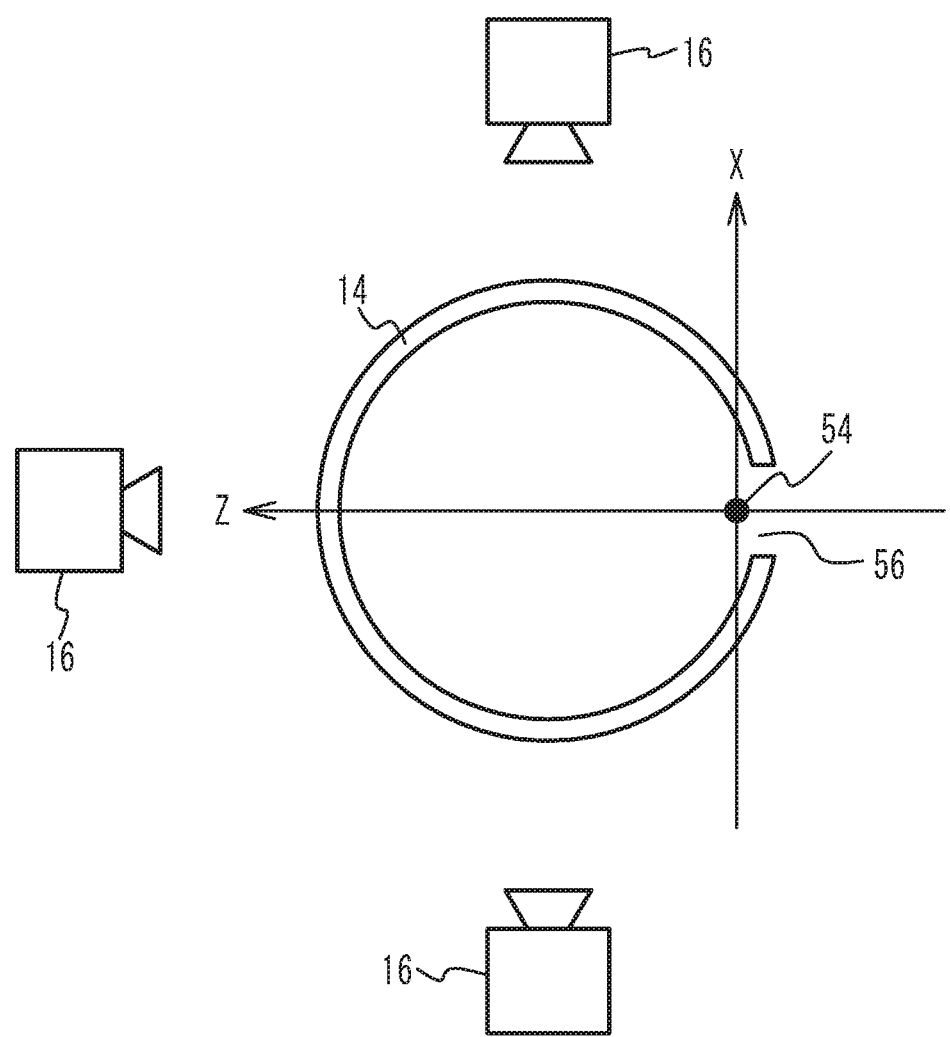
FIG. 6 is a top view of another example of the target projection unit.

The shape of the target projection unit 14 is not limited to a complete hemispherical shape, and it is sufficient if the target projection unit 14 has a substantially hemispherical shape. A substantially hemispherical shape includes a spherical shape or a shape of a substantial sphere of which a part opens. FIG. 6 is a top view of another example of the target projection unit 14. As illustrated in FIG. 6, the target projection unit 14 may have a shape formed of half or more of a spherical surface and having an aperture 56 having a size equal to or larger than at least the size of the pupil. In this case, since the projection region of the inspection image projected on the target projection unit 14 can be widened, the imaging unit 16 may be provided at the lateral sides in addition to the back side of the target projection unit 14.

Figure 7:
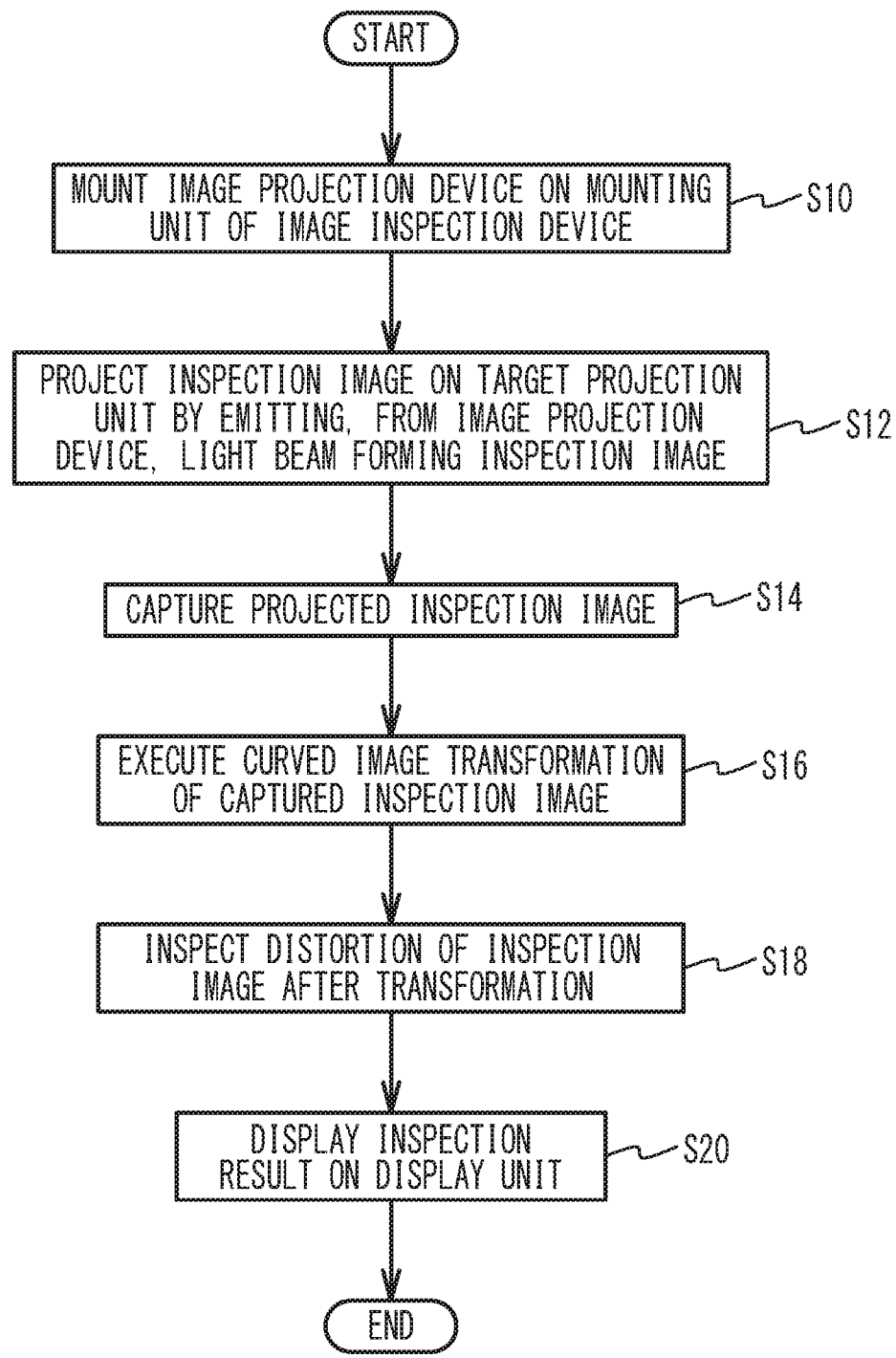
FIG. 7 is a flowchart illustrating an inspection method for inspecting distortion of an image.

FIG. 7 is a flowchart illustrating an inspection method for inspecting the distortion of an image. As illustrated in FIG. 7, the user mounts the image projection device 30, which is subject to the distortion inspection of an image, on the mounting unit 10 of the image inspection device 100 (step S10).

Then, the control unit 18 of the image inspection device 100 inputs the inspection image data to the control unit 44 of the image projection device 30 to cause the light beam 50 forming an inspection image to be emitted from the image projection device 30, thereby projecting the inspection image on the target projection unit 14 (step S12). The light beam 50 emitted from the image projection device 30 is emitted to the target projection unit 14 through the condensing lens 12, and the inspection image is thereby projected on the target projection unit 14. For example, a lattice image can be used as the inspection image.

Then, the control unit 18 captures the inspection image projected on the target projection unit 14 with the imaging unit 16 (step S14). The inspection image captured by the imaging unit 16 is transmitted to the control unit 18.

Then, the control unit 18 executes curved image transformation that transforms the captured inspection image from the polar coordinate system expressed by the moving radius from the center point of the hemispherical shape of the target projection unit 14 and the angle into the Cartesian coordinate system (step S16). Here, the curved image transformation is described. FIG. 8A through FIG. 8C are diagrams for describing the curved image transformation. FIG. 8A illustrates the imaging direction of the imaging unit 16, FIG. 8B illustrates the inspection image captured by the imaging unit 16, and FIG. 8C illustrates the inspection image after the curved image transformation. As illustrated in FIG. 8A, the inspection image is captured by the imaging unit 16 from the back side of the target projection unit 14. Since the target projection unit 14 has a surface in the shape of a hemisphere, the inspection image captured by the imaging unit 16 becomes an image that curves in a barrel-shape as illustrated in FIG. 8B. Here, as illustrated in FIG. 8A, the axis that is parallel to the imaging direction of the imaging unit 16 and passes through a center point 58 of the hemisphere of the target projection unit 14 is defined as a z-axis, the lateral direction of the projected inspection image is defined as an x-axis, and the longitudinal direction of the projected inspection image is defined as a y-axis. In this case, the position of the light beam 50 forming the inspection image captured by the imaging unit 16 is expressed by the polar coordinate system using the moving radius r from the center point 58 of the target projection unit 14, the angle $\theta 2$ from the z-axis, and the angle $\varphi 2$ from the x-axis. The polar coordinate system can be transformed into the Cartesian coordinate system by $x=r \sin \theta \cos \varphi$, $y=r \sin \theta \sin \varphi$, and $z=r \cos \theta$. The transformation into the Cartesian coordinate system transforms the inspection image curving in a barrel-shape as illustrated in FIG. 8B into the inspection image as illustrated in FIG. 8C. This transformation is referred to as the curved image transformation.

Then, the control unit 18 inspects distortion of the inspection image after the curved image transformation (hereinafter, may be referred to as a transformed inspection image) (step S18). The image after the curved image transformation is an image equivalent to the image to be viewed by the user wearing the image projection device 30. Thus, the distortion (geometric uniformity) of the image to be viewed by the user wearing the image projection device 30 can be inspected by inspecting the distortion of the transformed inspection image (the image of FIG. 8C).

FIG. 9A through FIG. 10B are diagrams for describing tangible examples of the distortion inspection. In FIG. 9A through FIG. 10B, bold lines express the transformed inspection image, and thin lines express the inspection image data input to the control unit 44 of the image projection device 30.

Figure 9A:
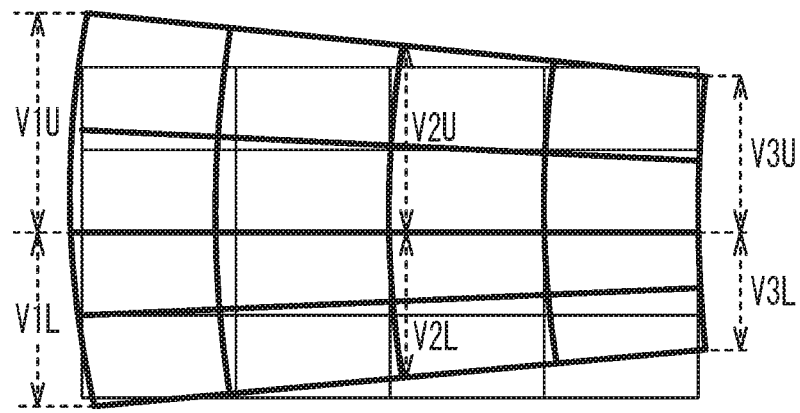
FIG. 9A through FIG. 9C are diagrams (No. 1) for describing a tangible example of a distortion inspection.

FIG. 9A is a diagram for describing the inspection of distortion in the vertical direction. As illustrated in FIG. 9A, the control unit 18 measures lengths V1U through V3L that are lengths from the central horizontal line, which is located at the center among the horizontal lines of the transformed inspection image, to the upper side and the lower side at the left side, the right side, and the center between them of the transformed inspection image. The length is measured by using the intersection coordinates of a lattice frame. Then, the control unit 18 inspects imbalance in the vertical direction by calculating Vbal1=(V1U−V1L)/(V1U+V1L)×100 (%), Vbal2=(V2U−V2L)/(V2U+V2L)×100(%), and Vbal3=(V3U−V3L)/(V3U+V3L)×100(%). In addition, the control unit 18 inspects difference in size in the vertical direction between the right side and the left side by calculating Vsize=((V1U+V1L)−(V3U+V3L))/(V2U+V2L)×100(%).

Figure 9B:
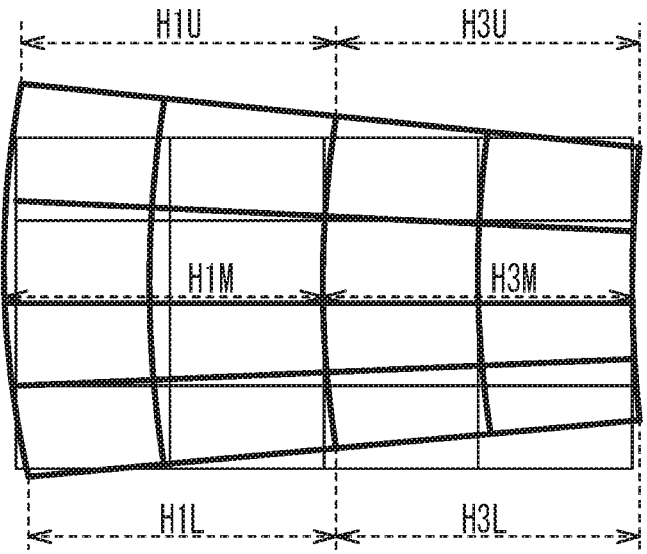

FIG. 9B is a diagram for describing the inspection of distortion in the horizontal direction. As illustrated in FIG. 9B, the control unit 18 measures lengths H1U through H3L that are lengths from the central vertical line, which is located at the center among the vertical lines of the transformed inspection image, to the left side and the right side at the upper side, the lower side, and the middle between them of the transformed inspection image. Then, the control unit 18 inspects imbalance in the horizontal direction by calculating HbalU=(H1U−H3U)/(H1U+H3U)×100(%), HbalM=(H1M−H3M)/(H1M+H3M)×100(%), and HbalL=(H1L−H3L)/(H1L+H3L)×100(%). The control unit 18 inspects difference in size in the horizontal direction between the top and the bottom by calculating Hsize=((H1U+H3U)−(H1L+H3L))/(H1M+H3M)×100(%).

Figure 9C:
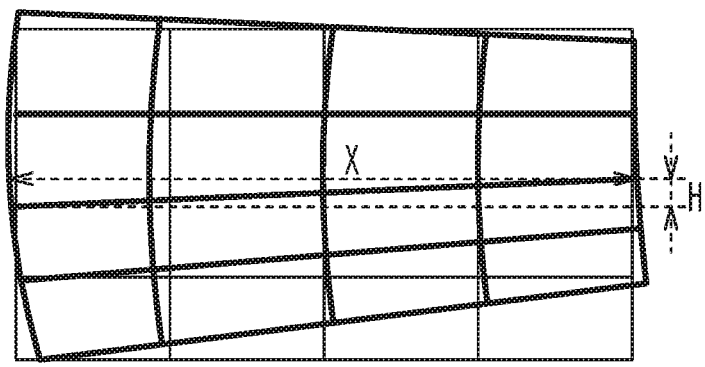

FIG. 9C is a diagram for describing the inspection of the slope of the horizontal line. As illustrated in FIG. 9C, the control unit 18 measures the distance H in the vertical direction (the upper/lower direction) between the point at which the central horizontal line of the transformed inspection image intersects with the left side of the transformed inspection image and the point at which the central horizontal line of the transformed inspection image intersects with the right side of the transformed inspection image. In addition, the control unit 18 measures the distance X in the horizontal direction (the right/left direction) from the point at which the central horizontal line of the transformed inspection image intersects with the right side of the transformed inspection image to the left side of the transformed inspection image. Then, the control unit 18 inspects the slope of the horizontal line by calculating HOLT=A TAN (H/X) (rad).

Figure 10A:
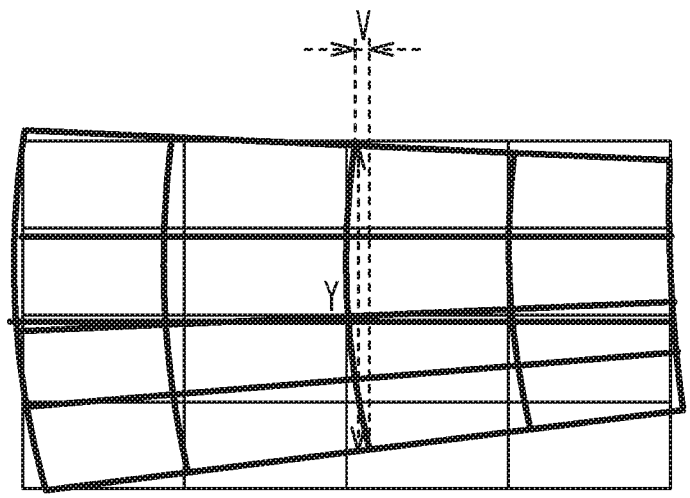
FIG. 10A and FIG. 10B are diagrams (No. 2) for describing the tangible example of the distortion inspection.

FIG. 10A is a diagram for describing the inspection of the slope of the vertical line. As illustrated in FIG. 10A, the control unit 18 measures the distance V in the horizontal direction (the right/left direction) between the point at which the central vertical line of the transformed inspection image intersects with the upper side of the transformed inspection image and the point at which the central vertical line of the transformed inspection image intersects with the lower side of the transformed inspection image. In addition, the control unit 18 measures the distance Y in the vertical direction (the upper/lower direction) from the point at which the central vertical line of the transformed inspection image intersects with the upper side of the transformed inspection image to the lower side of the transformed inspection image. Then, the control unit 18 inspects the slope of the vertical line by calculating VERT=A TAN(V/Y) (rad).

Figure 10B:
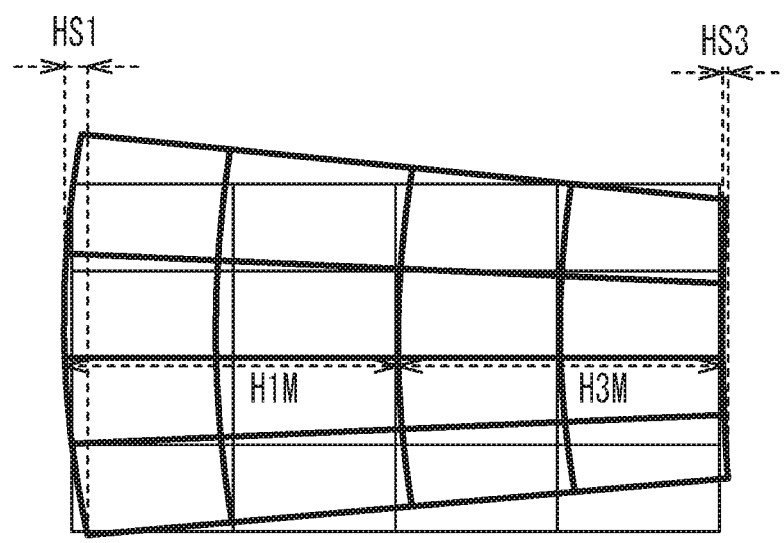

FIG. 10B is a diagram for describing the inspection of the curvature. As illustrated in FIG. 10B, the control unit 18 measures, at the left side of the transformed inspection image, the distance HS1 between the point at which the central horizontal line of the transformed inspection image intersects with the left side and one of the upper and lower edges that is further away in the horizontal direction from the point at which the central horizontal line intersects with the left side, and measures, at the right side of the transformed inspection image, the distance HS3 between the point at which the central horizontal line of the transformed inspection image intersects with the right side and one of the upper and lower edges that is further away in the horizontal direction from the point at which the central horizontal line intersects with the right side. In addition, the control unit 18 measures, at the middle between the upper side and the lower side of the transformed inspection image, the length H1M from the central vertical line of the transformed inspection image to the left side, and the length H3M from the central vertical line of the transformed inspection image to the right side. Then, the control unit 18 inspects the curvature by calculating S1=HS1/H1M×100(%) and S3=HS3/H3M×100(%).

Then, the control unit 18 displays the inspection results of distortion of the image (e.g., distortions described in FIG. 9A through FIG. 10B) on the display unit 24 (step S20). The control unit 18 may refer to the allowable range for the distortion amount preliminarily stored in the memory, determine whether the inspection result exceeds the allowable range, and display the determination result on the display unit 24.

As described above, the image inspection device 100 of the first embodiment includes the condensing lens 12 that condenses the light beam 50 emitted from the image projection device 30 mounted on the mounting unit 10, the target projection unit 14 that is irradiated with the light beam 50 that has been condensed and on which the inspection image is projected, and the inspection unit 22 that inspects the projected inspection image. That is, the inspection image is projected on the target projection unit 14 by emitting the light beam 50 forming the inspection image from the image projection device 30, causing the light beam 50 to pass through the condensing lens 12 to be emitted to the target projection unit 14, and the projected inspection image is then inspected. Accordingly, inspection of the image to be projected by the image projection device 30 that directly projects an image on the retina of the user becomes possible.

In addition, in the first embodiment, the target projection unit 14 has a substantially hemisphere shape having an opening at the condensing lens 12 side, and includes the imaging unit 16 that captures the inspection image projected on the target projection unit 14, and the image transformation unit 20 that transforms the captured inspection image from the polar coordinate system, which is expressed by the moving radius from the center point of the substantial hemisphere and the angle, into the Cartesian coordinate system. The inspection unit 22 inspects the inspection image that has been transformed by the image transformation unit 20. As described above, the condensing lens 12 and the substantially hemispherical target projection unit 14 constitute a pseudo eye (a dummy eye). Accordingly, the image equivalent to the image to be viewed by the user wearing the image projection device 30 can be inspected by capturing the inspection image projected on the target projection unit 14, transforming the captured inspection image from the polar coordinate system, which is expressed by the moving radius from the center point of a substantial hemisphere and the angle, into the Cartesian coordinate system, and inspecting the transformed inspection image.

In the first embodiment, the target projection unit 14 allows the inspection image to pass therethrough, and the imaging unit 16 captures the inspection image that has passed through the target projection unit 14. The above described configuration reduces the number of components of the image inspection device 100, and enables to inspect the image with simple structure.

Second Embodiment

The first embodiment describes an example in which the distortion of an image is inspected, while a second embodiment will describe an example in which the resolution of an image is inspected. In the second embodiment, the image inspection device is the same as the image inspection device 100 of the first embodiment, and the description thereof is thus omitted.

Figure 11:
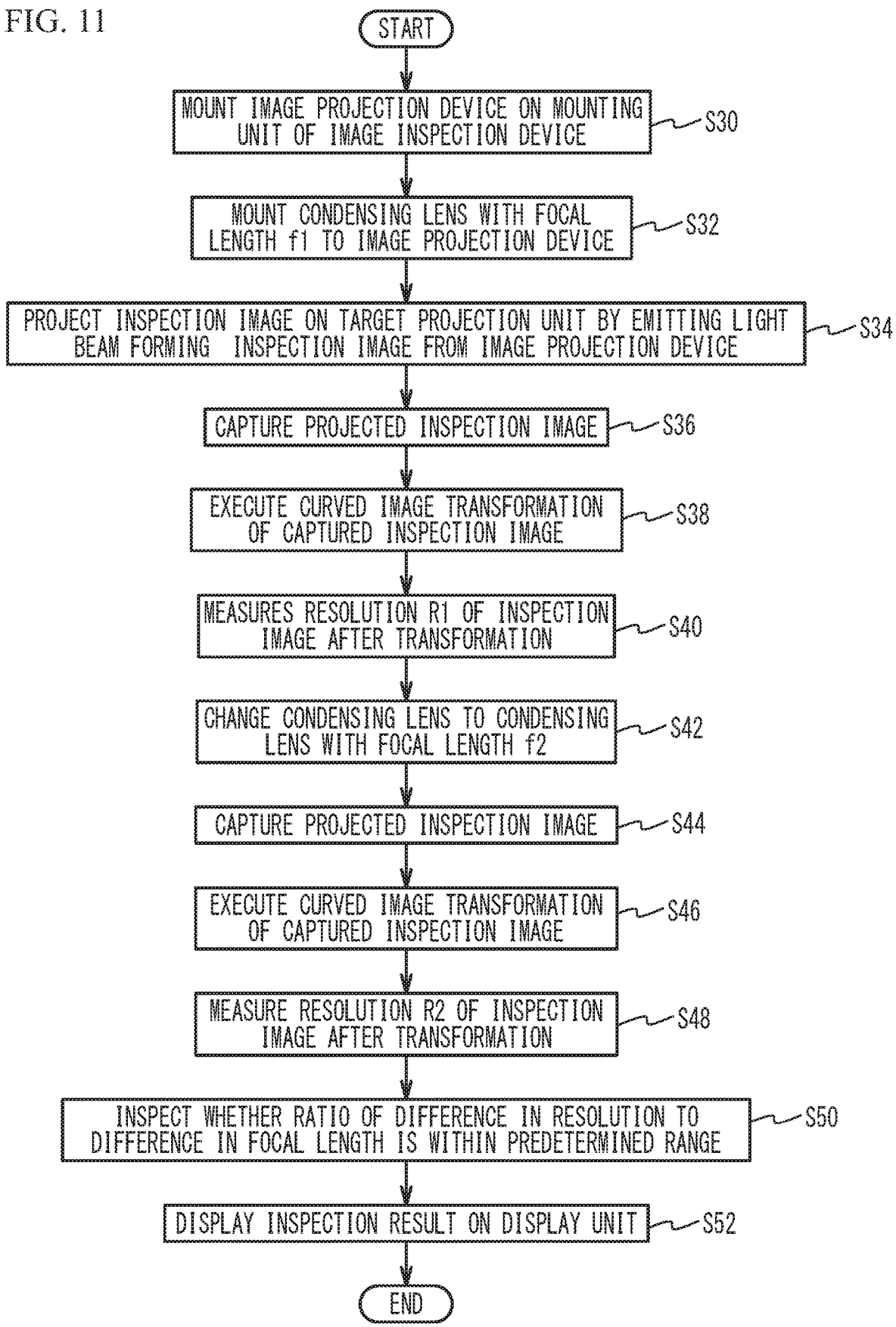
FIG. 11 is a flowchart illustrating a first example of an inspection method for inspecting the resolution of an image.
Figure 12A:
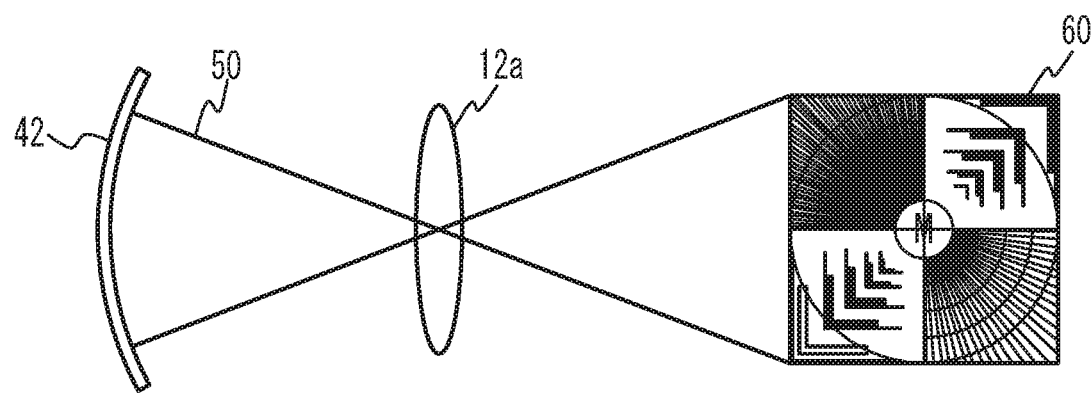
FIG. 12A and FIG. 12B are diagrams for describing the first example of the inspection method of the resolution of an image.
Figure 12B:
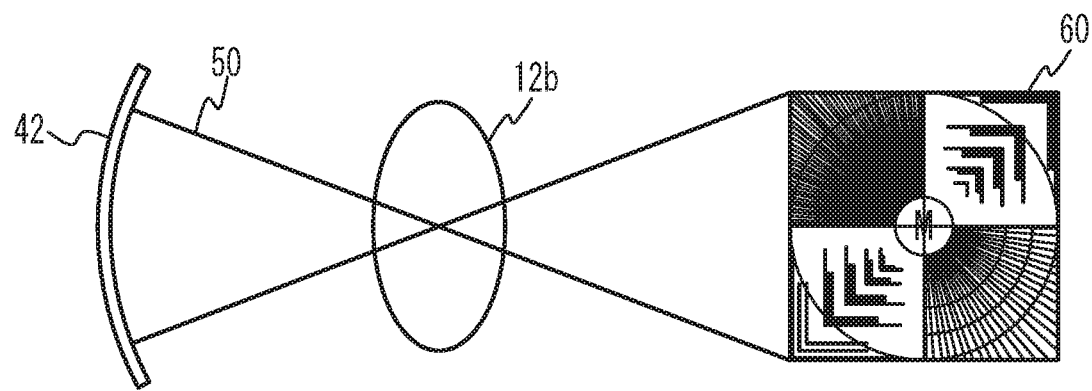

FIG. 11 is a flowchart illustrating a first example of an inspection method for inspecting the resolution of an image. FIG. 12A and FIG. 12B are diagrams for describing the first example of the inspection method of the resolution of an image. As illustrated in FIG. 11, the user mounts the image projection device 30 that is subject to the inspection for inspecting the resolution of an image on the mounting unit 10 of the image inspection device 100 (step S30). The user mounts a condensing lens 12a having a focal length f1 as the condensing lens of the image inspection device 100 (step S32).

Then, the control unit 18 of the image inspection device 100 inputs the inspection image data to the control unit 44 of the image projection device 30 to cause the light beam 50 forming the inspection image to be emitted from the image projection device 30, thereby projecting the inspection image on the target projection unit 14 (step S34). A resolution chart image can be used as the inspection image, for example. That is, as illustrated in FIG. 12A, an inspection image 60 of, for example, the resolution chart is projected by the light beam 50 passing through the condensing lens 12a with the focal length f1 and being emitted to the target projection unit 14.

Then, the control unit 18 captures the inspection image 60 projected on the target projection unit 14 with the imaging unit 16 (step S36). Then, the control unit 18 executes the curved image transformation of the captured inspection image 60 (step S38). Then, the control unit 18 measures the resolution R1 of the inspection image 60 after the curved image transformation (step S40).

After the measurement of the resolution R1 is completed, the user replaces the condensing lens 12a with the focal length f1 that is mounted to the image inspection device 100 with a condensing lens 12b with a focal length f2 that is different from the focal length f1, for example, is shorter than the focal length f1 (step S42). Accordingly, as illustrated in FIG. 12B, the inspection image 60 of the resolution chart is projected by the light beam 50 passing through the condensing lens 12b of the focal length f2 and being emitted to the target projection unit 14.

Then, the control unit 18 captures the inspection image 60 projected on the target projection unit 14 with the imaging unit 16 (step S44). Then, the control unit 18 executes the curved image transformation of the captured inspection image 60 (step S46). Then, the control unit 18 measures the resolution R2 of the inspection image 60 after the curved image transformation (step S48).

Then, the control unit 18 calculates the ratio ($\Delta R/\Delta f$) of the difference between the resolution R1 and the resolution R2 ($\Delta R = R1 - R2$) to the difference between the focal length f1 and the focal length f2 ($\Delta f = f1 - f2$), and inspects whether the ratio is within a predetermined range preliminarily stored in the memory (step S50). The control unit 18 display the inspection result on the display unit 24 (step S52).

As described above, in the second embodiment, the resolution R1 of the inspection image formed of the light beam 50 condensed by the condensing lens 12a with the focal length f1 and the resolution R2 of the inspection image formed of the light beam 50 condensed by the condensing lens 12b with the focal length f2 are measured. The resolution R1 and the resolution R2 correspond to retina image resolutions. Then, it is inspected whether the ratio of the difference between the resolution R1 and the resolution R2 to the difference between the focal length f1 and the focal length f2 is within the predetermined range. When the ratio is within the predetermined range, it is considered that the focal depth is deep, and therefore, the favorable image can be provided to the user regardless of the difference among users wearing the image projection device 30. Accordingly, the resolution independent from the focal point (the focal point independent resolution) of the image to be projected by the image projection device 30 that directly projects the image on the retina of the user can be measured, and it can be inspected whether the image projection device 30 can provide a favorable image to the user regardless of the difference among users, in the second embodiment. Thus, the condensing lens 12a with the focal length f1 preferably has a condensing point in a position anterior to the target projection unit 14, and the condensing lens 12b with the focal length f2 has a condensing point in a position posterior to the target projection unit 14.

Third Embodiment

A third embodiment describes a second example in which the resolution of an image is inspected. Also in the third embodiment, the image inspection device is the same as the image inspection device 100 of the first embodiment, and the description thereof is thus omitted.

Figure 13:
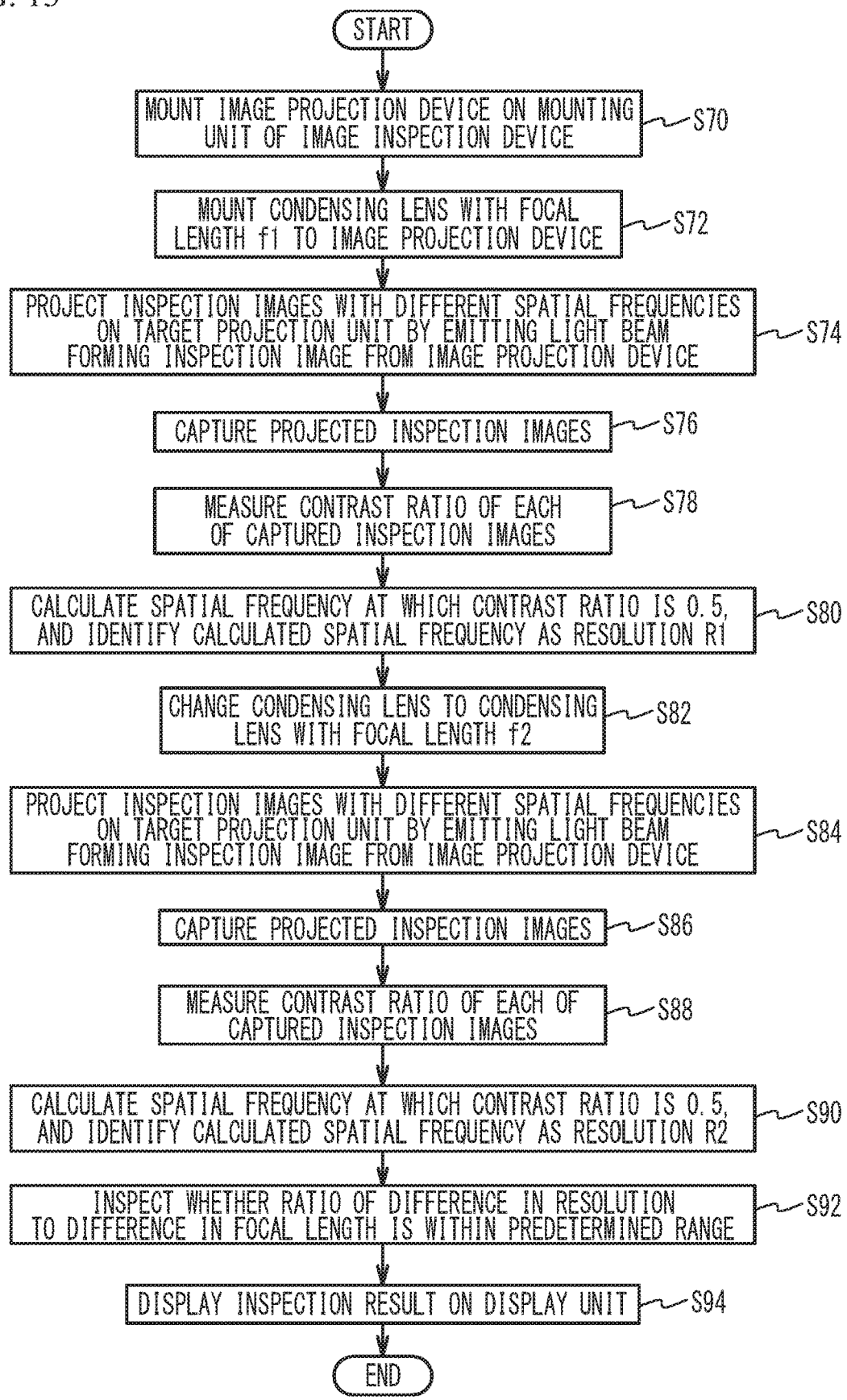
FIG. 13 is a flowchart illustrating a second example of the inspection method for inspecting the resolution of an image.

FIG. 13 is a flowchart illustrating a second example of the inspection method for inspecting the resolution of an image. FIG. 14A through FIG. 15B are diagrams for describing the second example of the inspection method of the resolution of an image. As illustrated in FIG. 13, the user mounts the image projection device 30 that is subject to the inspection for inspecting the resolution of an image on the mounting unit 10 of the image inspection device 100 (step S70). The user mounts the condensing lens 12a with the focal length f1 as the condensing lens of the image inspection device 100 (step S72).

Then, the control unit 18 of the image inspection device 100 inputs a plurality of inspection image data sets having different spatial frequencies to the control unit 44 of the image projection device 30, causes the light beam 50 forming the inspection image to be emitted from the image projection device 30, thereby projecting a plurality of inspection images having different spatial frequencies on the target projection unit 14 (step S74). An image in which a bright section and a dark section are alternately repeated can be used as the inspection image, for example. Then, the control unit 18 captures the inspection images projected on the target projection unit 14 with the imaging unit 16 (step S76). That is, as illustrated in FIG. 14A, the inspection images 60 with different spatial frequencies are projected by the light beam 50 passing through the condensing lens 12a with the focal length f1. In each of the inspection images 60, the dimensions of a bright section 62 and a dark section 64 are the same, and the dimensions of the bright section 62 and the dark section 64 differ among the inspection images 60.

FIG. 14A also presents graphs of the output intensities of the imaging unit 16 that captures the inspection images 60 with different spatial frequencies.

Figure 15A:
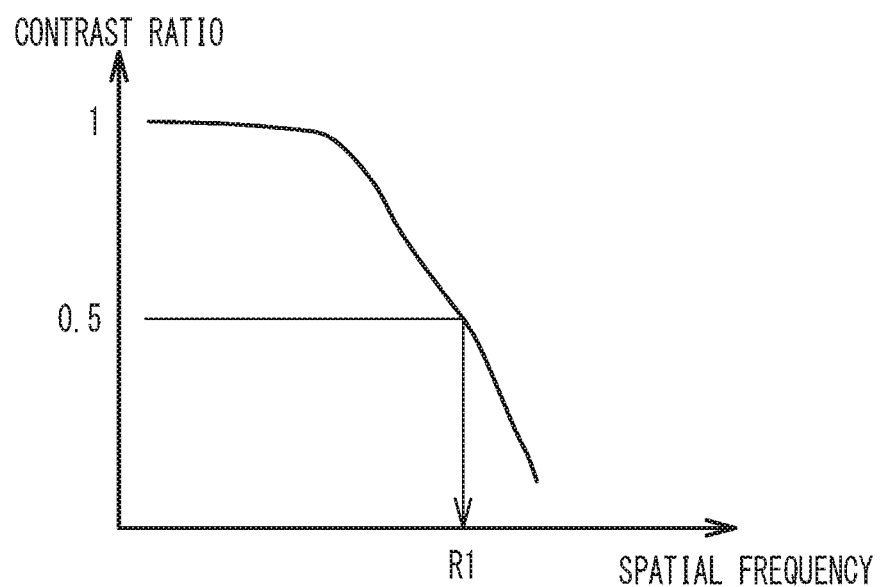
FIG. 15A and FIG. 15B are diagrams (No. 2) for describing the second example of the inspection method of the resolution of an image.

Then, the control unit 18 measures the contrast ratio of each of the captured inspection images 60 (step S78). Then, the control unit 18 calculates the spatial frequency at which the contrast ratio is 0.5, and identifies the calculated spatial frequency as the resolution R1 (step S80). That is, the relationship between the spatial frequency and the contrast ratio as illustrated in FIG. 15A is obtained by measuring the contrast ratio of each of the inspection images 60 with different spatial frequencies, and the spatial frequency at which the contrast ratio is 0.5 is identified as the resolution R1 based on the relationship.

After the identification of the resolution R1 is completed, the user replaces the condensing lens 12a having the focal length f1 mounted to the image inspection device 100 with the condensing lens 12b with the focal length f2 that is different from the focal length f1, for example, is shorter than the focal length f1 (step S82). Then, the control unit 18 inputs a plurality of inspection image data sets having different spatial frequencies to the control unit 44 of the image projection device 30, causes the light beam 50 forming the inspection image to be emitted from the image projection device 30, thereby projecting the inspection images with different spatial frequencies on the target projection unit 14 (step S84). Accordingly, the inspection images 60 with different spatial frequencies are projected by the light beam 50 passing through the condensing lens 12b with the focal length f2 as illustrated in FIG. 14B.

Figure 15B:
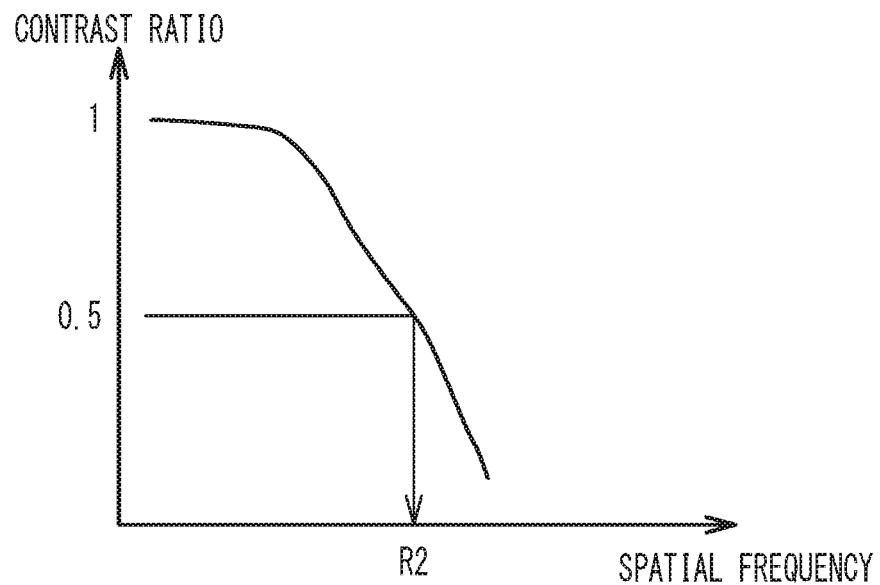

Then, the control unit 18 captures the inspection images 60 projected on the target projection unit 14 with the imaging unit 16 (step S86). Then, the control unit 18 measures the contrast ratio of each of the captured inspection images 60 (step S88). Then, the control unit 18 calculates the spatial frequency at which the contrast ratio is 0.5, and identifies the calculated spatial frequency as the resolution R2 (step S90). That is, the relationship between the spatial frequency and the contrast ratio as illustrated in FIG. 15B is obtained, and the spatial frequency at which the contrast ratio is 0.5 is identified as the resolution R2 based on the relationship.

Then, the control unit 18 calculates the ratio ($\Delta R/\Delta f$) of the resolution between the resolution R1 and the resolution R2 ($\Delta R=R1-R2$) to the difference between the focal length f1 and the focal length f2 ($\Delta f=f1-f2$), and inspects whether the ratio is within a predetermined range preliminarily stored in the memory (step S92). The control unit 18 displays the inspection result on the display unit 24 (step S94).

As described above, in the third embodiment, the spatial frequency at which the contrast ratio is 0.5 is identified as the resolution R1 with use of the inspection images with different spatial frequencies formed of the light beam 50 condensed by the condensing lens 12a with the focal length f1. In the same manner, the spatial frequency at which the contrast ratio is 0.5 is identified as the resolution R2 with use of the inspection images with different spatial frequencies formed of the light beam 50 condensed by the condensing lens 12b with the focal length f2. Then, it is inspected whether the ratio of the resolution between the resolution R1 and the resolution R2 to the difference between the focal length f1 and the focal length f2 is within the predetermined range. Accordingly, as in the second embodiment, the resolution independent from the focal length (the focal length independent resolution) of the image to be projected by the image projection device 30, which directly projects the image on the retina of the user, can be measured, and it can be inspected whether the image projection device 30 can provide a favorable image to the user regardless of the difference among users.

Figure 16:
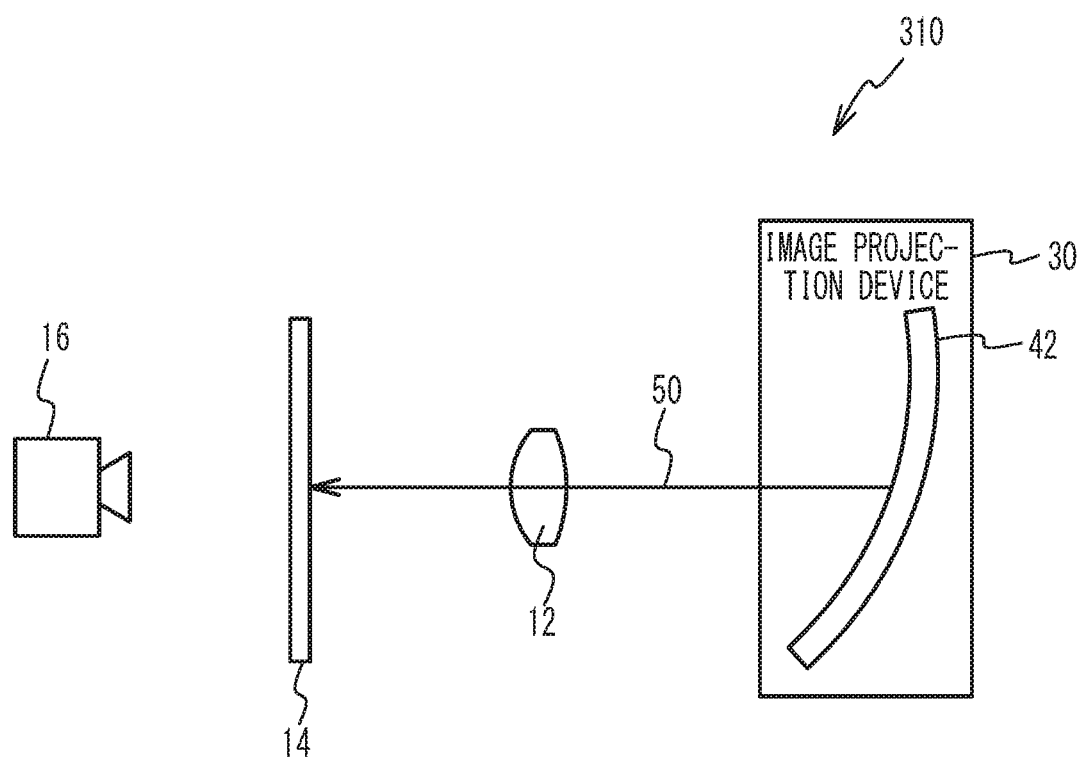
FIG. 16 illustrates an image inspection device in accordance with a first variation of a third embodiment.

A first variation of the third embodiment describes a third example in which the resolution of an image is inspected. FIG. 16 illustrates an image inspection device 310 in accordance with the first variation of the third embodiment. As illustrated in FIG. 16, in the image inspection device 310 of the first variation of the third embodiment, the target projection unit 14 has a planar shape. The imaging unit 16 captures an image passing through the planar target projection unit 14. Other structures are the same as those of the image inspection device 100 of the first embodiment, and the description thereof is thus omitted.

Figure 17:
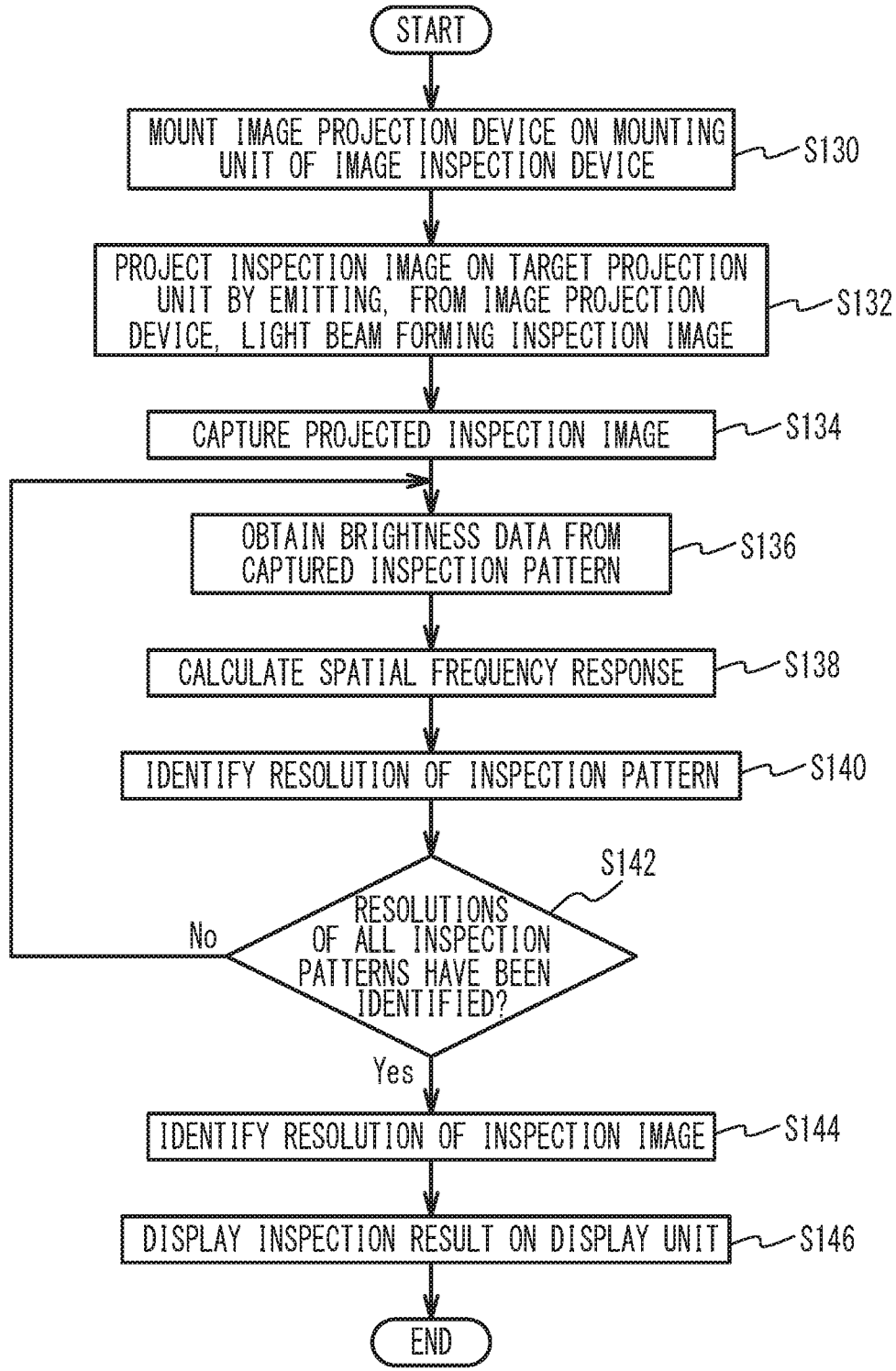
FIG. 17 is a flowchart illustrating a third example of the inspection method for inspecting the resolution of an image.

FIG. 17 is a flowchart illustrating the third example of the inspection method for inspecting the resolution of an image. FIG. 18A through FIG. 20C are diagrams for describing the third example of the inspection method of the resolution of an image. As illustrated in FIG. 17, the user mounts the image projection device 30 that is subject to the inspection for inspecting the resolution of an image on the mounting unit 10 of the image inspection device 100 (step S130).

Figure 18A:
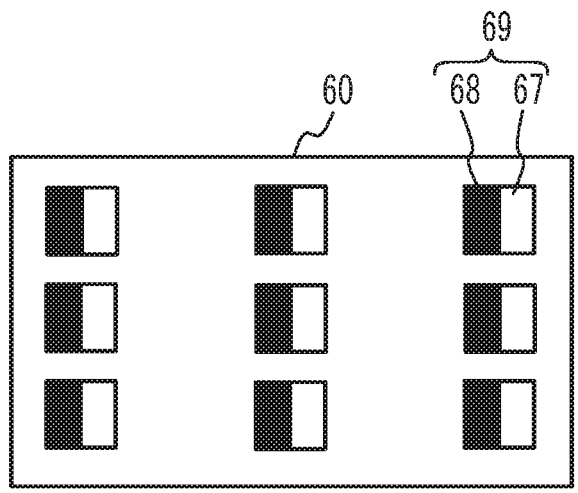
FIG. 18A and FIG. 18B are diagrams (No. 1) for describing the third example of the inspection method of the resolution of an image.
Figure 18B:
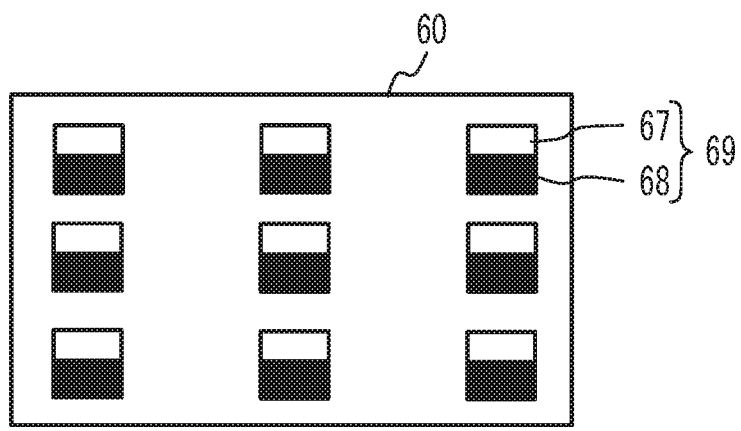

Then, the control unit 18 of the image inspection device 100 inputs the inspection image data to the control unit 44 of the image projection device 30 to cause the light beam 50 forming the inspection image to be emitted from the image projection device 30, thereby projecting the inspection image 60 on the target projection unit 14 (step S132). FIG. 18A and FIG. 18B illustrate examples of the inspection image 60 to be projected on the target projection unit 14. The inspection image 60 includes a plurality of inspection patterns 69 each having a stripe white pattern 67 and a stripe black pattern 68. Formed in the inspection pattern 69 are the white pattern 67 of 50 pixels and the black pattern 68 of 50 pixels. The white pattern 67 and the black pattern 68 may be longitudinal patterns or lateral patterns.

Figure 19:
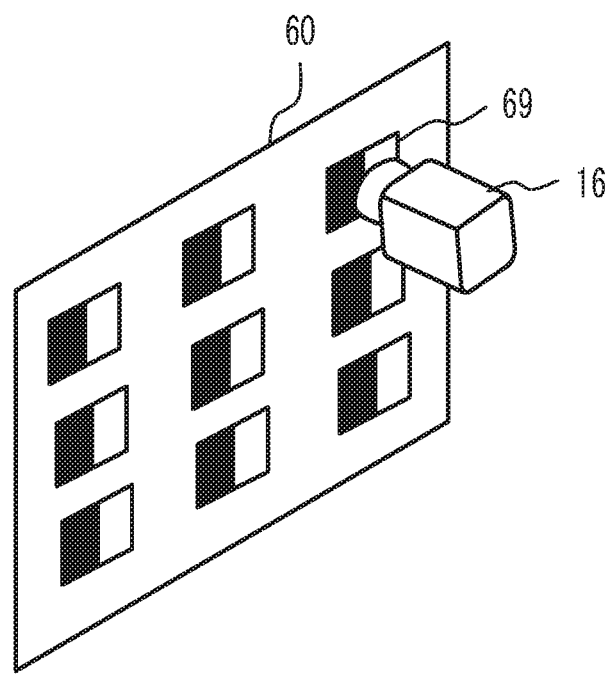
FIG. 19 is a diagram (No. 2) for describing the third example of the inspection method of the resolution of an image.

Then, the control unit 18 captures the inspection image 60 projected on the target projection unit 14 with the imaging unit 16 (step S134). That is, as illustrated in FIG. 19, the control unit 18 captures the inspection pattern 69 included in the inspection image 60 projected on the target projection unit 14 by using the imaging unit 16.

Figure 20A:
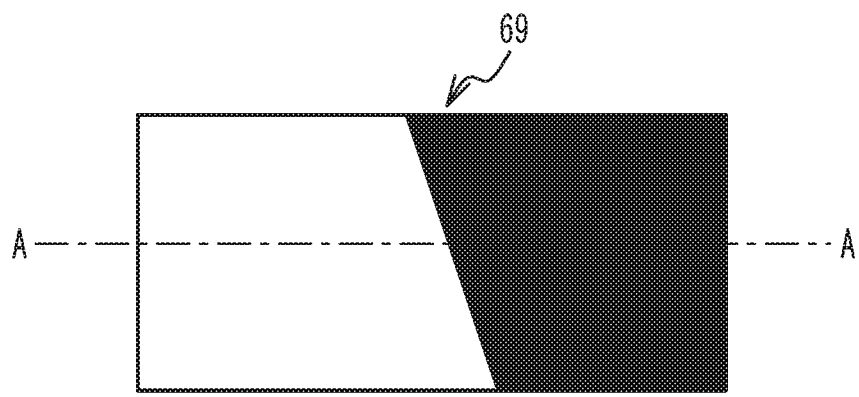
FIG. 20A through FIG. 20C are diagrams (No. 3) for describing the third example of the inspection method of the resolution of an image.
Figure 20B:
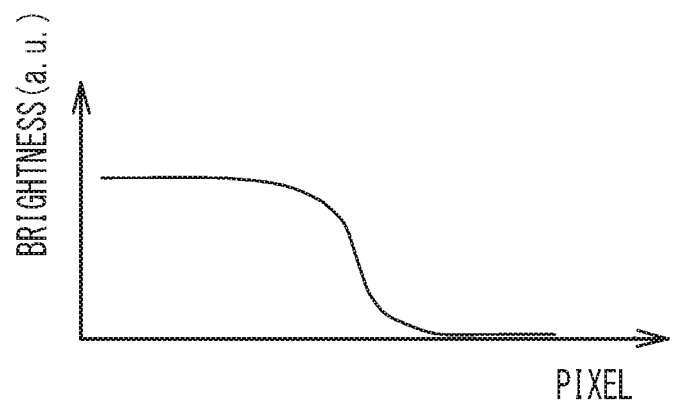

Then, the control unit 18 obtains the brightness data from the inspection pattern 69 captured by the imaging unit 16 (step S136). For example, the brightness data of the inspection pattern 69 as illustrated in FIG. 20B is obtained from the inspection pattern 69 captured by the imaging unit 16 as illustrated in FIG. 20A. FIG. 20B illustrates an example of the brightness data along line A-A in FIG. 20A, and the horizontal axis represents the pixel, and the vertical axis represents the brightness.

Figure 20C:
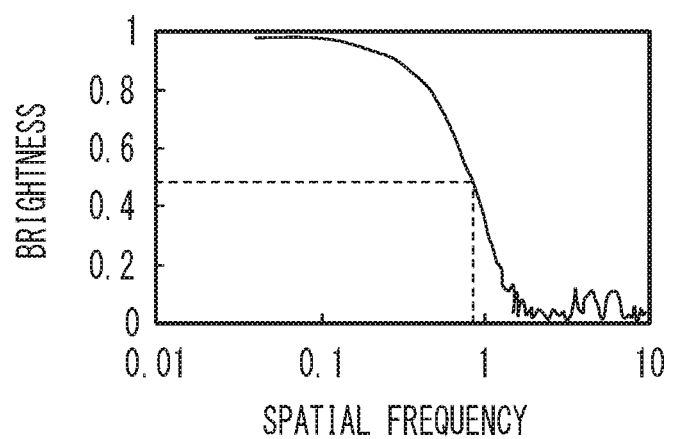

Then, the control unit 18 calculates the spatial frequency response (SFR) from the brightness data of the inspection pattern 69 (step S138). For example, the spatial frequency response characteristic as illustrated in FIG. 20C is obtained from the brightness data of the inspection pattern 69. The horizontal axis in FIG. 20C represents the spatial frequency f (1/pixel). The vertical axis represents the brightness, and stark white is represented by 1 and jet black is represented by 0.

Then, the control unit 18 identifies the resolution of the inspection pattern 69 from the spatial frequency response characteristic (step S140). For example, the control unit 18 calculates the spatial frequency at which the brightness is 0.5, and identifies the calculated spatial frequency as the resolution.

Then, the control unit 18 determines whether the resolutions of all the inspection patterns 69 contained in the inspection image 60 have been identified (step S142). When there is the inspection pattern 69 of which the resolution is not identified yet (step S142: No), the control unit 18 returns to step S136. When the resolutions of all the inspection patterns 69 have been identified (step S142: Yes), the control unit 18 identifies the resolution of the inspection image 60 (step S144). For example, the control unit 18 identifies the average of the resolutions of the inspection patterns 69 as the resolution of the inspection image 60. The control unit 18 may identify the maximum value of the resolutions of the inspection patterns 69 as the resolution of the inspection image 60, or may identify the minimum value as the resolution of the inspection image 60. Then, the control unit 18 displays the inspection result of the resolution on the display unit 24 (step S146).

Fourth Embodiment

Figure 21:
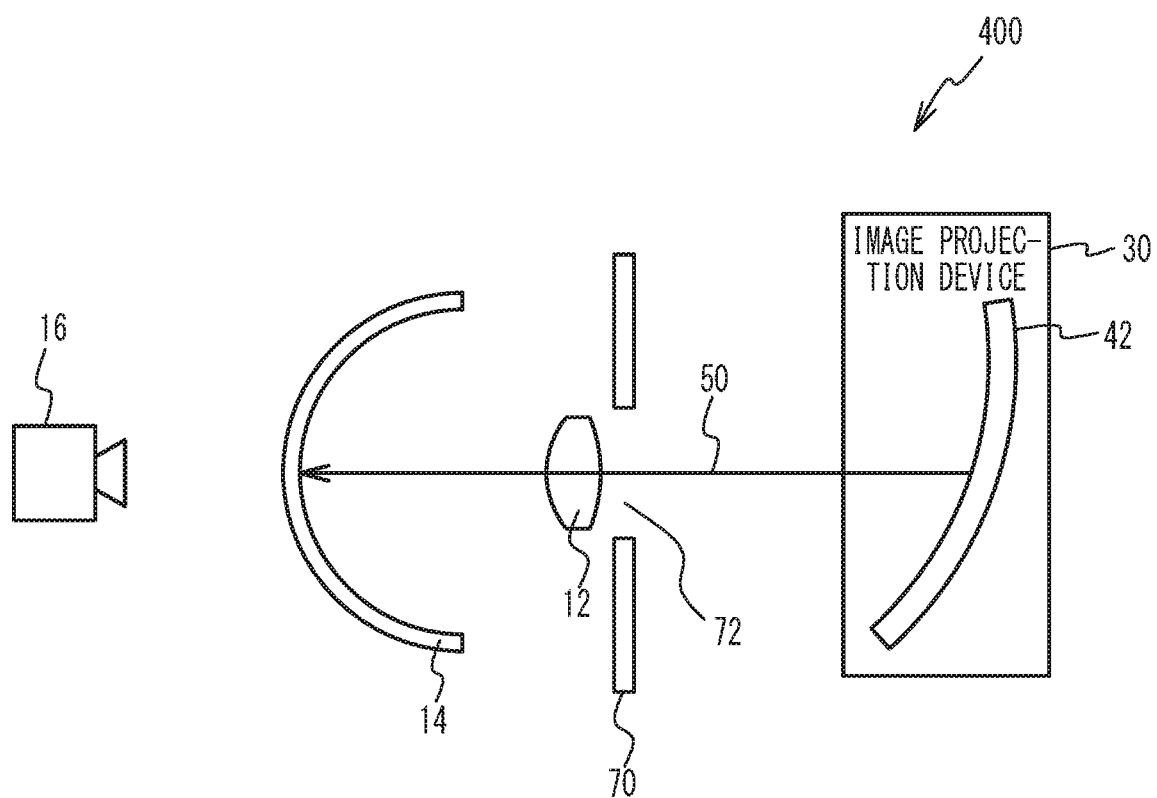
FIG. 21 illustrates an image inspection device in accordance with a fourth embodiment.

A fourth embodiment describes an example in which the brightness and the pattern shape of an image are inspected. FIG. 21 illustrates an image inspection device 400 in accordance with the fourth embodiment. As illustrated in FIG. 21, the image inspection device 400 of the fourth embodiment includes an apertured plate 70 that is located near the condensing lens 12 and interposed between the condensing lens 12 and the projection unit 42 of the image projection device 30. The apertured plate 70 has an aperture 72, which is a circular opening portion through which the light beam 50 passes, near the condensing lens 12. The apertured plate 70 does not necessarily have a plate-like shape as long as the apertured plate 70 has a structure that blocks the light near the aperture 72, and may be referred to as an eye box. The apertured plate 70 is movable in the two-dimensional direction in the plane perpendicular to the optical axis of the condensing lens 12. The light beam 50 reflected by the projection unit 42 passes through the aperture 72 of the apertured plate 70, is condensed by the condensing lens 12, and is emitted to the target projection unit 14. The imaging unit 16 captures the image passing through the target projection unit 14. Other structures are the same as those of the image inspection device 100 of the first embodiment, and the description thereof is thus omitted.

Figure 22:
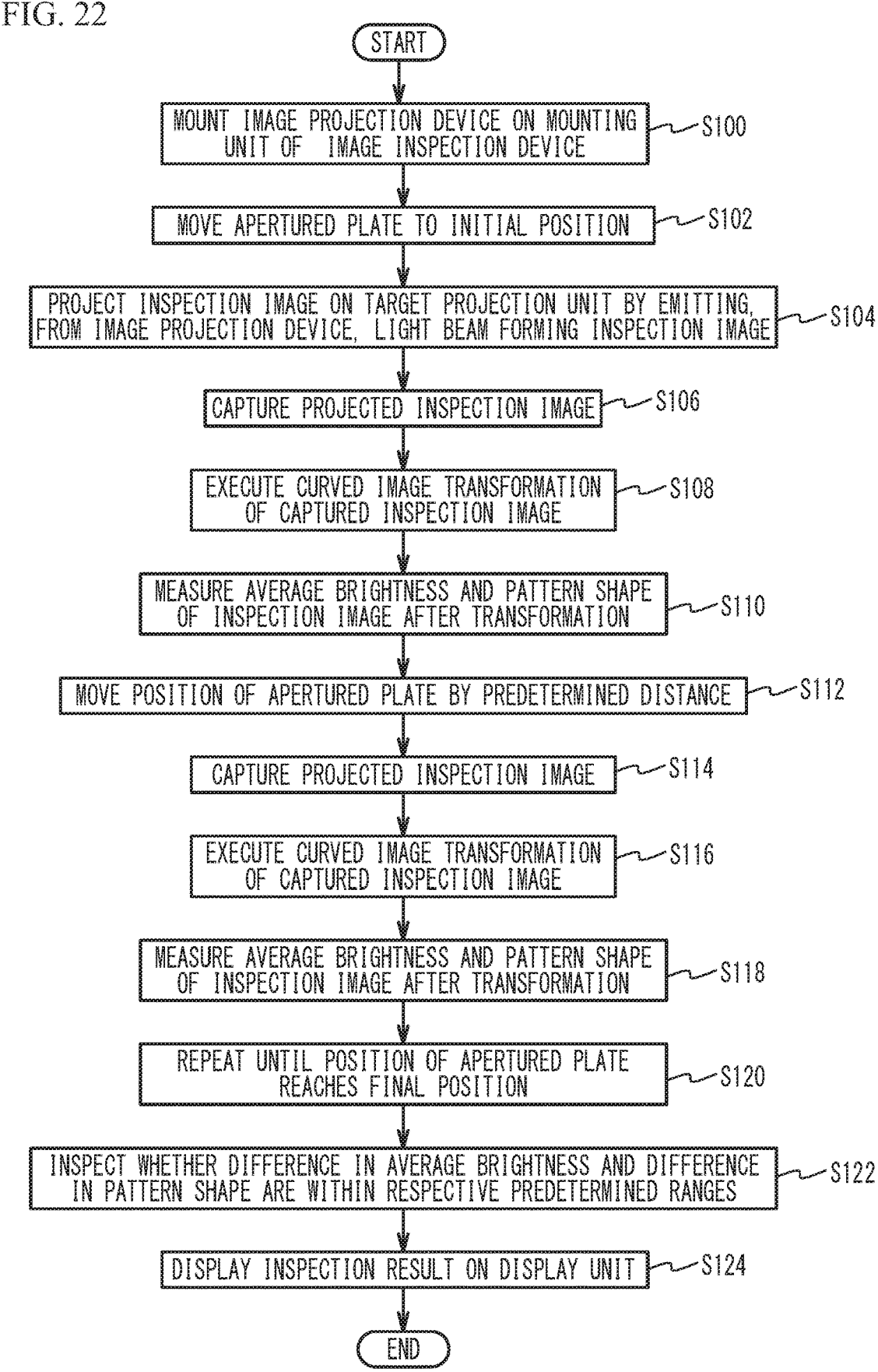
FIG. 22 is a flowchart illustrating an example of an inspection method for inspecting the brightness and the pattern shape of an image.

FIG. 22 is a flowchart illustrating an example of the inspection method for inspecting the brightness and the pattern shape of an image. FIG. 23A and FIG. 23B are diagrams for describing the inspection method of the brightness and the pattern shape of an image. As illustrated in FIG. 22, the user mounts the image projection device 30 that is subject to the inspection for inspecting the brightness and the pattern shape of an image on the mounting unit 10 of the image inspection device 400 (step S100). Then, the user moves the position of the apertured plate 70 to an initial position (step S102). For example, as illustrated in FIG. 23A, the position of the apertured plate 70 is moved so that a scanning light formed of the light beam 50 passes through the vicinity of the lower edge of the aperture 72 provided in the apertured plate 70.

Then, the control unit 18 of the image inspection device 400 inputs the inspection image data to the control unit 44 of the image projection device 30 to cause the light beam 50 forming the inspection image to be emitted from the image projection device 30, thereby projecting the inspection image on the target projection unit 14 (step S104). The inspection image 60 projected on the target projection unit 14 has a region 66 with decreased brightness due to the effect of the apertured plate 70 as illustrated in FIG. 23A. A lattice image described in the first embodiment can be used as the inspection image, for example.

Then, the control unit 18 captures the inspection image 60 projected on the target projection unit 14 with the imaging unit 16 (step S106). Then, the control unit 18 executes the curved image transformation of the captured inspection image 60 (step S108). Then, the control unit 18 measures the average brightness and the pattern shape (such as the width) of the inspection image 60 after the curved image transformation (step S110).

Then, the user moves the position of the apertured plate 70 by a predetermined distance (step S112). Then, the control unit 18 captures the inspection image 60 projected on the target projection unit 14 with the imaging unit 16 (step S114). Then, the control unit 18 executes the curved image transformation of the captured inspection image 60 (step S116). Then, the control unit 18 measures the average brightness and the pattern shape (such as the width) of the inspection image 60 after the curved image transformation (step S118). Until the position of the apertured plate 70 reaches the final position, step S112 through step S118 are repeated (step S120). For example, as illustrated in FIG. 23B, the position at which the scanning light formed of the light beam 50 passes through the vicinity of the upper edge of the aperture 72 provided in the apertured plate 70 is defined as the final position of the apertured plate 70. In this case, the inspection image 60 projected on the target projection unit 14 has the region 66 with decreased brightness due to the effect of the apertured plate 70.

The control unit 18 inspects whether the difference in measured average brightness among the inspection images 60 is within a predetermined range and the difference in pattern shape among the inspection images 60 is within a predetermined range (step S122). The control unit 18 displays the inspection result on the display unit 24 (step S124).

As described above, in the fourth embodiment, it is inspected whether the difference in average brightness and/or difference in pattern shape among images formed of the light beam 50 passing through the aperture 72 located at respective positions different from each other due to the movement of the apertured plate 70, which is inserted near the condensing lens 12, in the plane direction perpendicular to the optical axis of the condensing lens 12 is within a predetermined range. The aperture 72 of the apertured plate 70 is considered as the pupil of the user wearing the image projection device 30. Thus, when the difference in average brightness and/or the difference in pattern shape is within a predetermined range, it is considered that change in brightness of the image viewed by the user and/or change in pattern shape of the image viewed by the user is small even when the user wearing the image projection device 30 faces in various directions. Therefore, in the fourth embodiment, it can be inspected whether the image projection device 30 can provide an image of which change in brightness and/or change in pattern shape is small to the user even when the user wearing the image projection device 30 faces in different directions. Since the aperture 72 of the apertured plate 70 corresponds to the pupil, the apertured plate 70 is preferably located near the condensing lens 12 so as to model the positional relationship between the crystalline lens and the pupil.

The fourth embodiment describes a case where the user moves the position of the apertured plate 70 as an example, but a drive unit such as an actuator capable of moving the position of the apertured plate 70 may be provided, and the control unit 18 may move the position of the apertured plate 70 with use of the drive unit.

Fifth Embodiment

Figure 24:
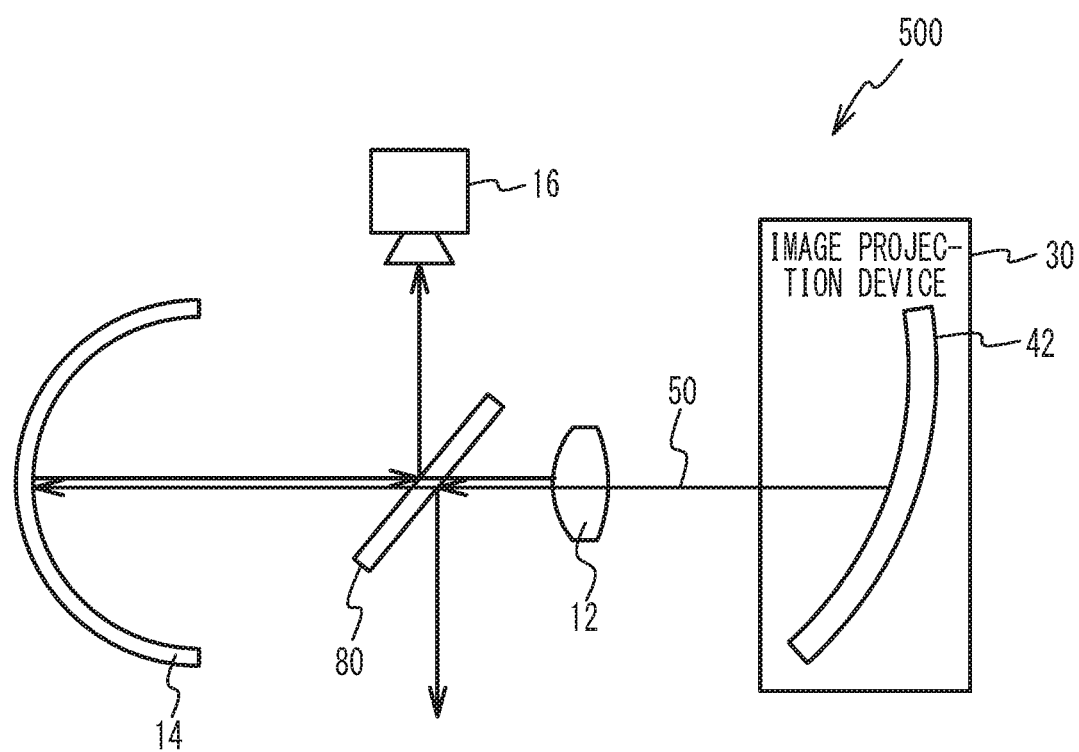
FIG. 24 illustrates an image inspection device in accordance with a fifth embodiment.

FIG. 24 illustrates an image inspection device 500 in accordance with a fifth embodiment. As illustrated in FIG. 24, the image inspection device 500 of the fifth embodiment includes a reflection system composed of a half mirror 80 on the light path of the light beam 50 between the condensing lens 12 and the target projection unit 14. The imaging unit 16 captures the inspection image projected on the target projection unit 14 and reflected by the target projection unit 14 and the half mirror 80. Other structures are the same as those of the image inspection device 100 of the first embodiment, and the description thereof is thus omitted.

When the inspection image passing through the target projection unit 14 is captured by the imaging unit 16 as in the first embodiment, there may be an effect of unnecessary light. On the other hand, as in the fifth embodiment, when the reflection system composed of the half mirror 80 is provided on the light path of the light beam 50 between the condensing lens 12 and the target projection unit 14 and the target projection unit 14 is made of a material with a high light-diffusion property, the effect of unnecessary light is reduced by capturing the inspection image reflected by the target projection unit 14 and the half mirror 80.

Sixth Embodiment

Figure 25:
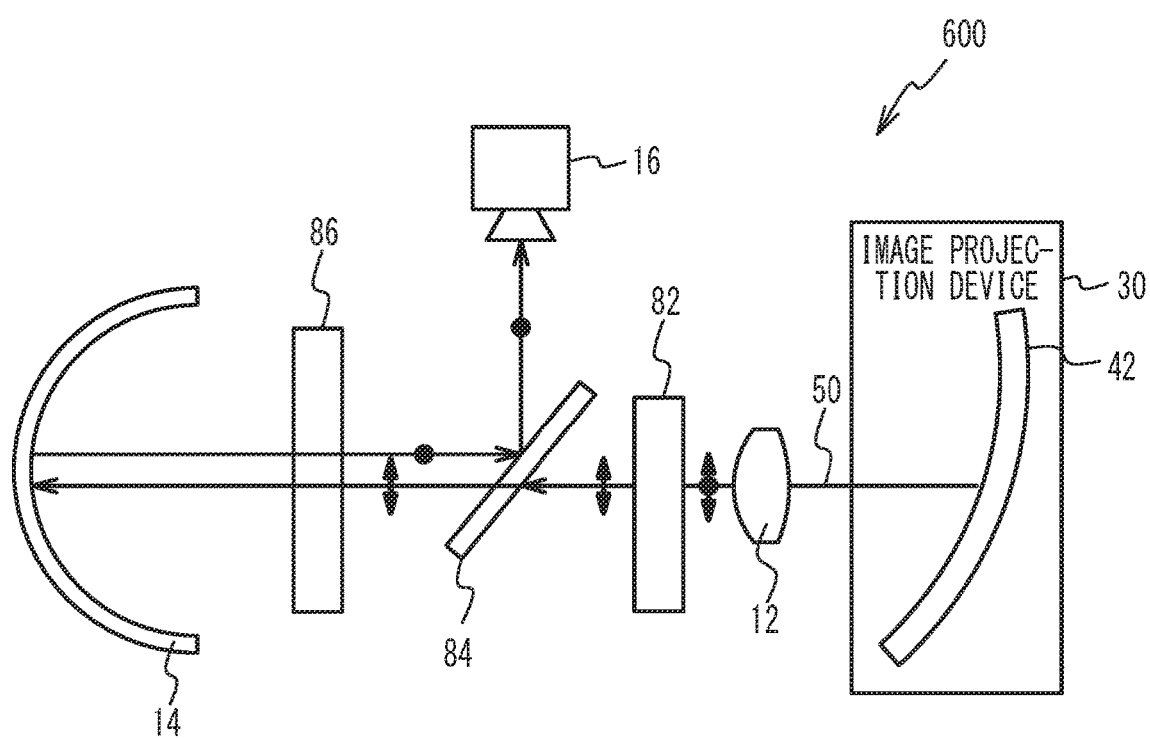
FIG. 25 illustrates an image inspection device in accordance with a sixth embodiment.

FIG. 25 illustrates an image inspection device 600 in accordance with a sixth embodiment. As illustrated in FIG. 25, the image inspection device 600 of the sixth embodiment has a reflection system composed of a polarizer 82, a polarization beam splitter 84, and a quarter wavelength plate 86 on the light path of the light beam 50 between the condensing lens 12 and the target projection unit 14. The imaging unit 16 captures the inspection image projected on the target projection unit 14 and reflected by the target projection unit 14 and the polarization beam splitter 84. In FIG. 25, the arrows on the light beam 50 indicate P-polarized light, and black circles indicate S-polarized light. Other structures are the same as those of the image inspection device 100 of the first embodiment, and the description thereof is thus omitted.

When the half mirror 80 is located between the condensing lens 12 and the target projection unit 14 as in the fifth embodiment, the amount of light entering the imaging unit 16 decreases. In contrast, as in the sixth embodiment, when the reflection system composed of the polarizer 82, the polarization beam splitter 84, and the quarter wavelength plate 86 is located on the light path of the light beam 50 between the condensing lens 12 and the target projection unit 14 and the inspection image reflected by the target projection unit 14 and the polarization beam splitter 84 is captured, the amount of light entering the imaging unit 16 is inhibited from being decreased.

Seventh Embodiment

Figure 26:
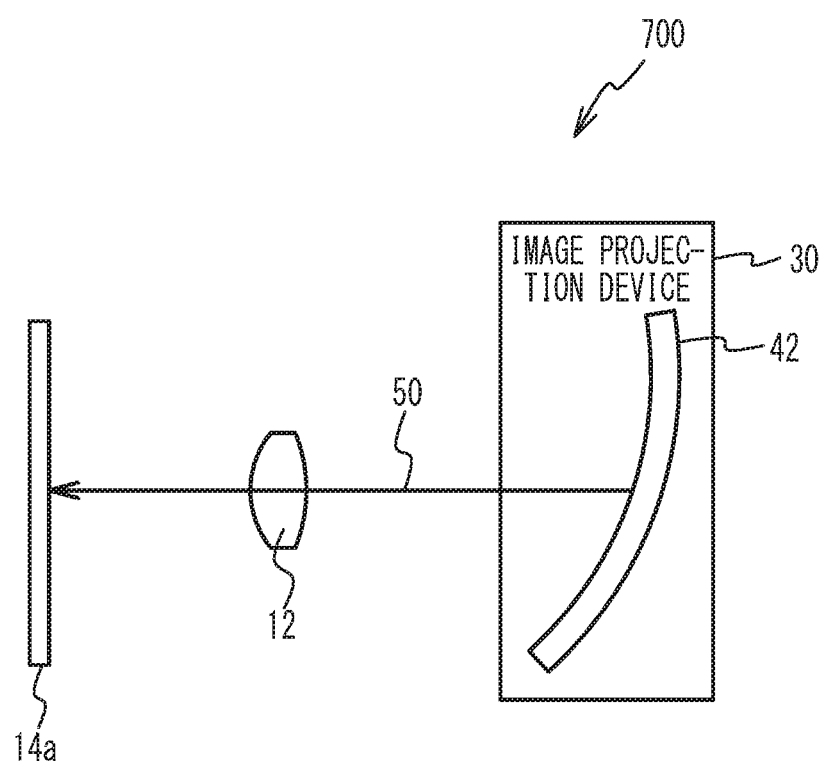
FIG. 26 illustrates an image inspection device in accordance with a seventh embodiment.

FIG. 26 illustrates an image inspection device 700 in accordance with a seventh embodiment. As illustrated in FIG. 26, the image inspection device 700 of the seventh embodiment is not provided with the imaging unit 16, and a target projection unit 14a is a detector having a planar shape. The target projection unit 14a is, for example, a CCD image sensor or a CMOS image sensor. Other structures are the same as those of the image inspection device 100 of the first embodiment, and the description thereof is thus omitted.

Figure 27:
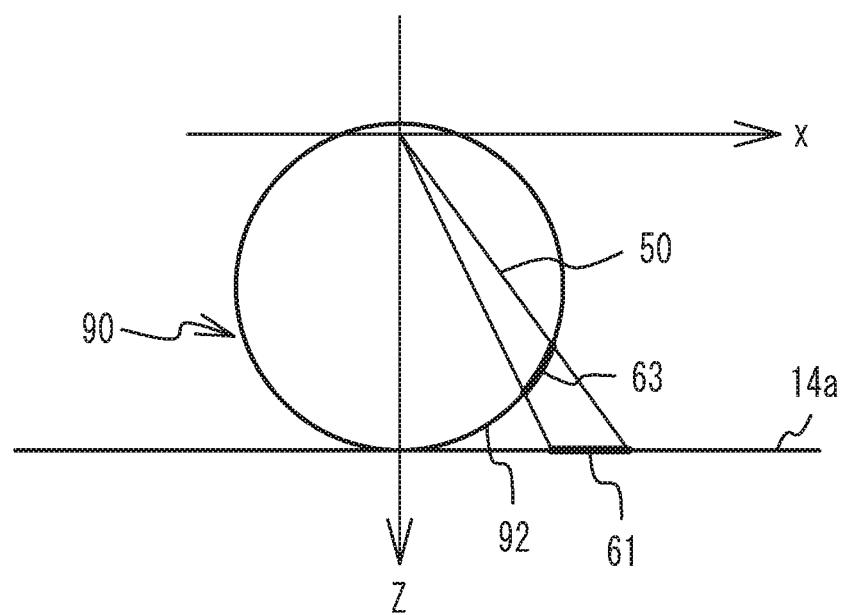
FIG. 27 illustrates the size of a light beam projected on the target projection unit having a planar shape.

FIG. 27 is a diagram for describing the size of the light beam 50 projected on the planar target projection unit 14a. As illustrated in FIG. 27, the size (spot size) 61 of the light beam 50 projected on the planar target projection unit 14a is greater than a size (spot size) 63 of the light beam 50 projected on the retina 92 of the eye ball 90.

The first through sixth embodiments describe the combination of the target projection unit 14 formed of glass and having a substantially hemispherical shape or a flat shape and the imaging unit 16, but a detector with a planar shape may be used as the target projection unit 14a as in the seventh embodiment. In this case, the inspection image can be inspected by detecting the inspection image projected on the target projection unit 14a by the light beam 50 emitted from the image projection device 30 and condensed by the condensing lens 12 with use of the target projection unit 14a.

The first through seventh embodiments describe a case where the distortion, the resolution, the brightness, and the pattern shape of an image are inspected as the inspection of the image as examples. However, at least one of the distortion, the resolution, the brightness, the pattern shape, the gamma characteristic, the contrast ratio, the aspect ratio, and the hue may be inspected. A conventionally known inspection method may be used as the inspection method. Hereinafter, examples of the inspection method will be described.

Figure 28:
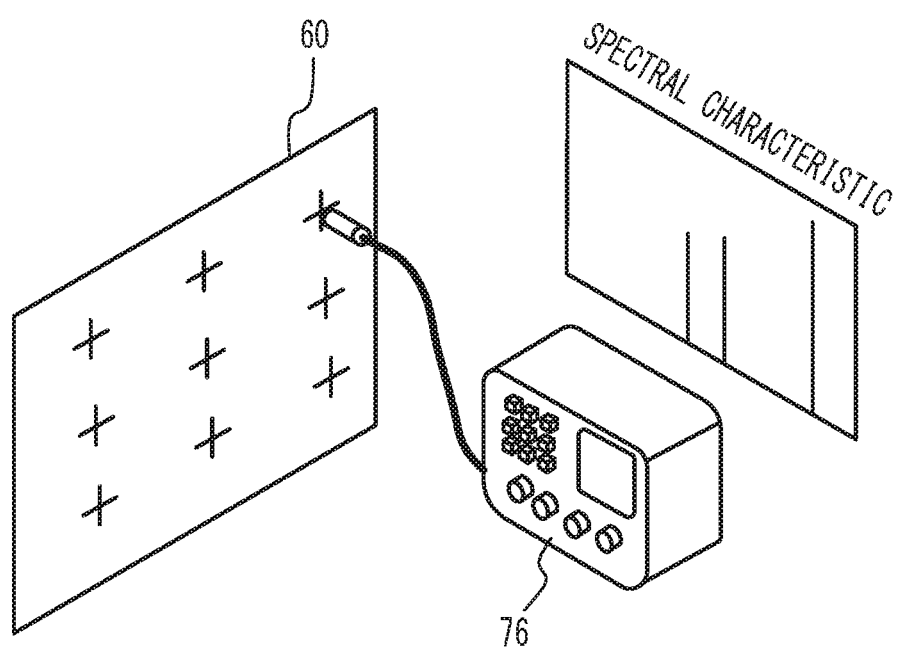
FIG. 28 illustrates an example of an inspection method of a gamma characteristic.

FIG. 28 illustrates an example of an inspection method of a gamma characteristic. As illustrated in FIG. 28, the color inspection image 60 formed with use of red, green, and blue is projected on the target projection unit 14. The spectra of red, green, and blue are measured at a plurality of points in the projected inspection image 60 with use of a spectroscope 76. Then, the gamma characteristic is calculated by using the chromaticity of each color obtained from the measured spectra. The above described inspection of the gamma characteristic may be performed by the control unit 18 or may be performed by both the control unit 18 and the user.

Figure 29:
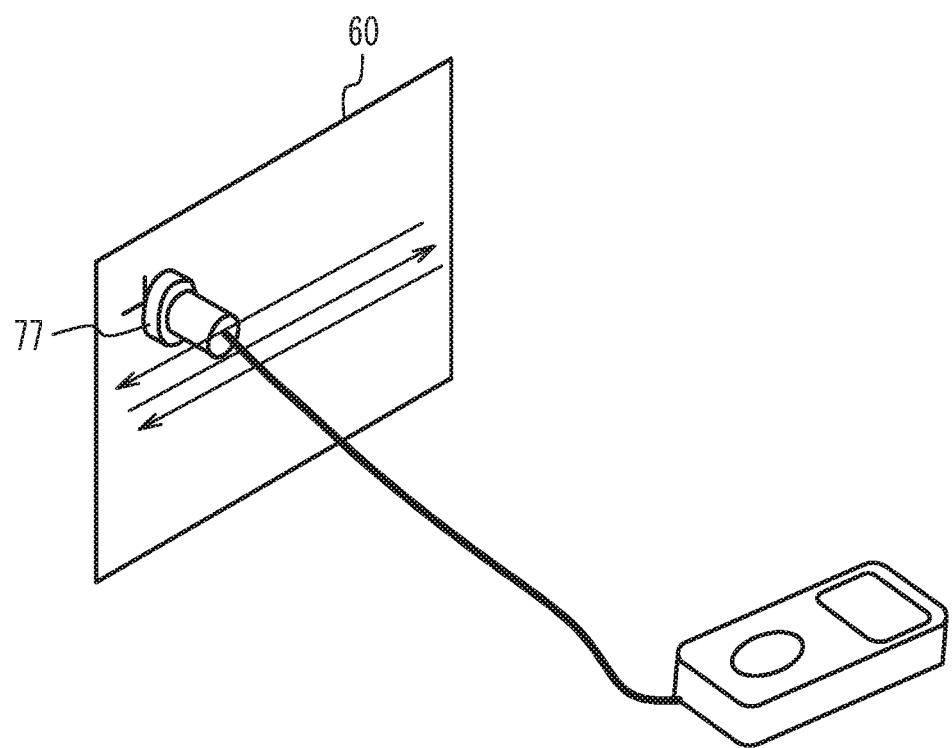
FIG. 29 illustrates an example of an inspection method of a contrast ratio.

FIG. 29 illustrates an example of an inspection method of a contrast ratio. As illustrated in FIG. 29, the inspection image 60 of which the entire region is white is projected on the target projection unit 14. Then, the illumination intensity of white is measured at a plurality of points in the projected inspection image 60 with use of an illuminance meter 77. Then, the inspection image 60 of which the entire region is black is projected on the target projection unit 14. Then, the illumination intensity of black is measured at a plurality of points in the projected inspection image 60 with use of the illuminance meter 77. Then, the contrast ratio is calculated by using the measured illuminance intensity of white and the measured illuminance intensity of black. The above-described inspection of the contrast ratio may be performed by the control unit 18, or may be performed by both the control unit 18 and the user.

Figure 30A:
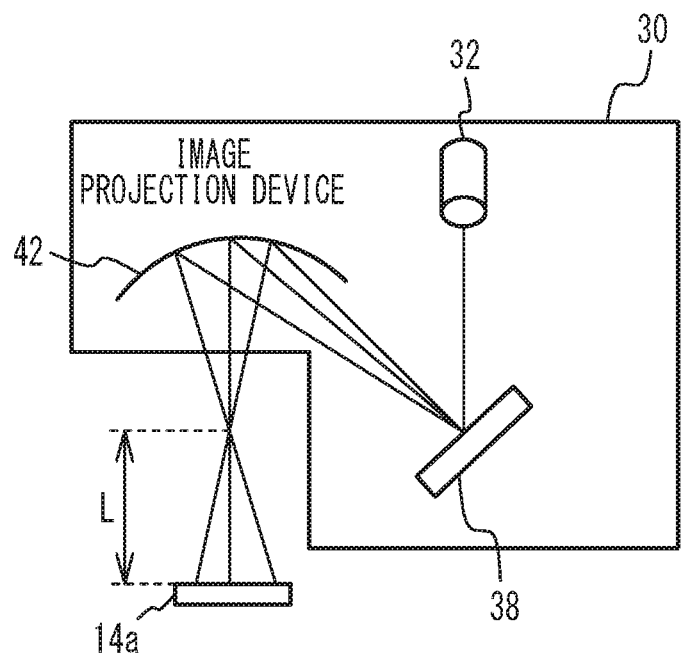
FIG. 30A and FIG. 30B are diagrams for describing an example of an inspection method of an aspect ratio.
Figure 30B:
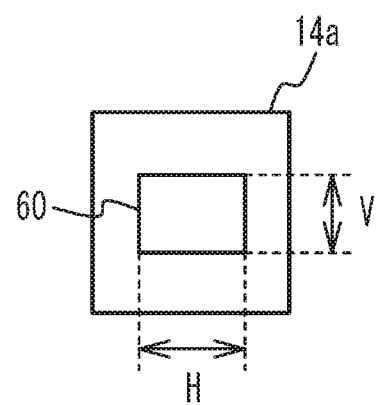

FIG. 30A and FIG. 30B illustrate an example of an inspection method of an aspect ratio. As illustrated in FIG. 30A and FIG. 30B, the inspection image 60 of which the entire region is white is projected on the target projection unit 14a. Then, the width H and the height V of the projected inspection image 60 are measured. Then, the field of view in the horizontal direction $FOV_H$ and the field of view in the vertical direction $FOV_V$ are calculated. The field of view in the horizontal direction $FOV_H$ is calculated by, for example, $FOV_H = 2 \tan^{-1}(H/2L)$, and the field of view in the vertical direction $FOV_V$ is calculated by, for example, $FOV_V = 2 \tan^{-1}(V/2L)$. L represents the distance from the convergence point of the scanning light to the target projection unit 14. The aspect ratio is calculated by calculating $FOV_H/FOV_V$. The above described inspection of the aspect ratio may be performed by the control unit 18, or may be performed by both the control unit 18 and the user. For example, the aspect ratio may be inspected by using a lattice image presented in the first embodiment as the inspection image and measuring the aspect ratio of the lattice. Alternatively, the inspection may be performed by measuring the ratio ($\varphi/\theta$) of the angle $\varphi 1$ to the angle $\theta 1$ illustrated in FIG. 4A and FIG. 4B.

Eighth Embodiment

Figure 31:
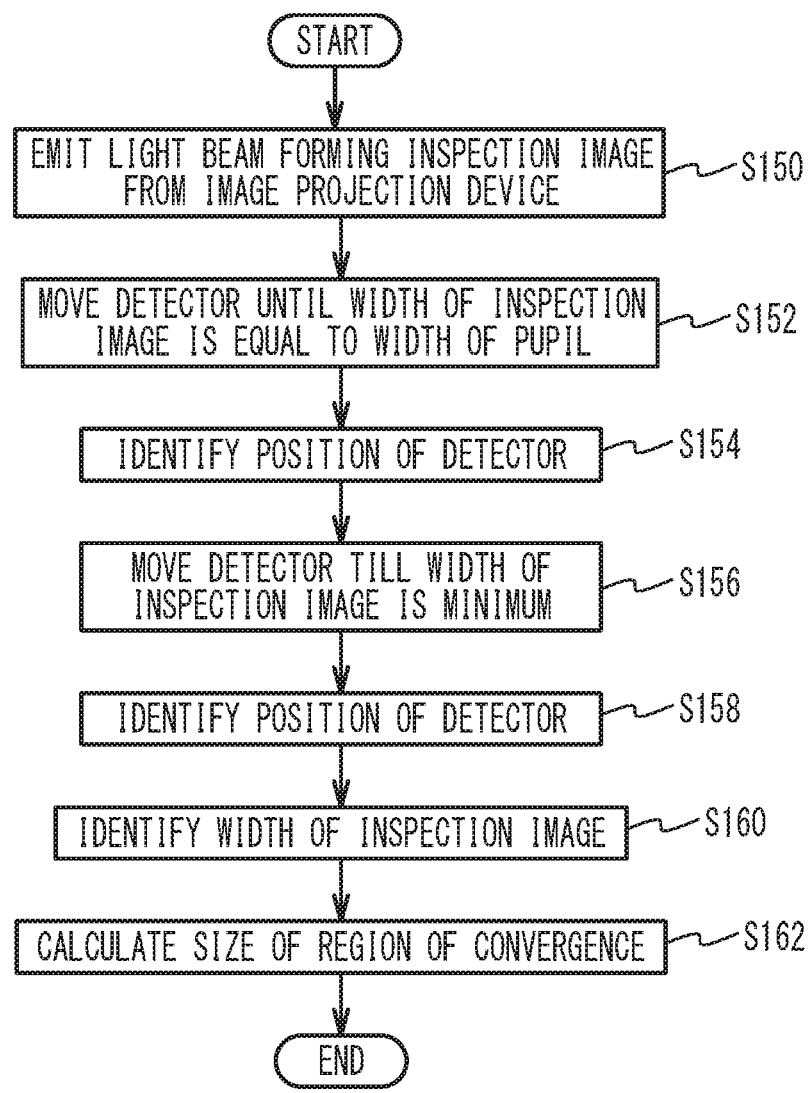
FIG. 31 is a flowchart illustrating an inspection method for inspecting a region of convergence of a scanning light.
Figure 32A:
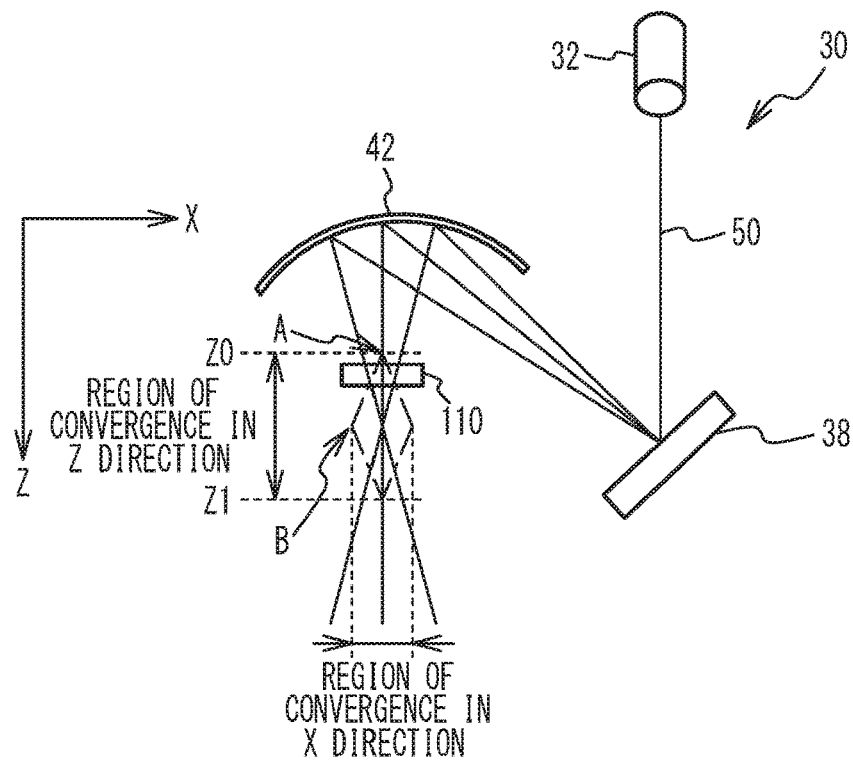
FIG. 32A through FIG. 32C are diagrams for describing the inspection method of the region of convergence of a scanning light.
Figure 32B:
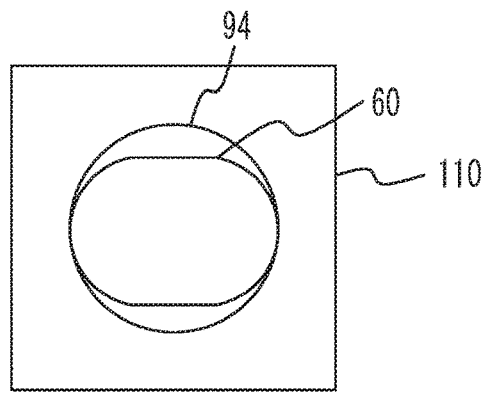
Figure 32C:
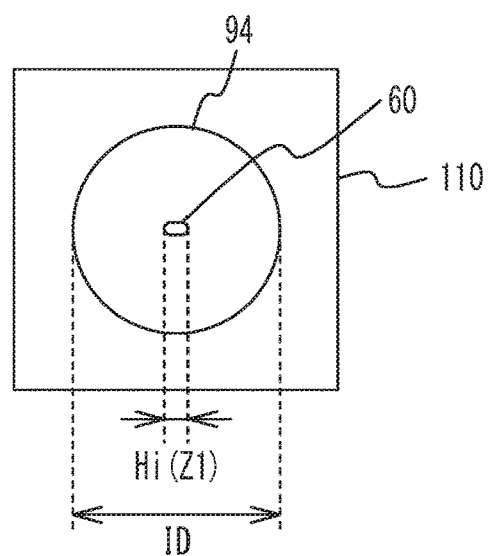

An eighth embodiment describes an example of an inspection of the region of convergence of a scanning light projected from the image projection device 30. FIG. 31 is a flowchart illustrating an example of an inspection method for inspecting the region of convergence of a scanning light. FIG. 32A through FIG. 32C are diagrams for describing the inspection method of the region of convergence of a scanning light. FIG. 32B illustrates the inspection image detected when a detector 110 that detects the inspection image is positioned at the point A in FIG. 32A, and FIG. 32C illustrates the inspection image detected when the detector 110 is positioned at the point B in FIG. 32A. Here, the detector 110 may be installed in the planar target projection unit 14a described in FIG. 16 of the third embodiment.

As illustrated in FIG. 31, the user causes the light beam 50 forming the inspection image to be emitted from the image projection device 30 (step S150). As illustrated in FIG. 32A, the light beam 50 is emitted from the image projection device 30, passes through the scanning unit 38 and the projection unit 42, and then projects an image on the detector 110. At this time, the condensing lens 12 may be located between the projection unit 42 and the detector 110 as in FIG. 3 and FIG. 16. Then, the user moves the position of the detector 110 in the direction away from the projection unit 42 of the image projection device 30 till the width of the inspection image detected by the detector 110, which is located posterior to the projection unit 42 in the light path of the light beam 50 and has a planar shape, is equal to the width of the pupil (step S152). That is, as illustrated in FIG. 32B, the position of the detector 110 is moved till the inspection image 60 having a width equal to the width of the pupil 94 is detected by the detector 110. Hereinafter, the direction away from the projection unit 42 of the image projection device 30 is defined as a Z direction, and the direction intersecting with the Z direction is defines as an X direction. When the detector 110 is located in the target projection unit 14a, the target projection unit 14a also moves together with the detector 110.

Then, the user identifies the position in the Z direction of the detector 110 when the width of the inspection image 60 becomes equal to the width of the pupil 94 as Z0 (step S154). Then, the user moves the position of the detector 110 in the Z direction till the width of the inspection image 60 detected by the detector 110 is minimum (step S156). That is, as illustrated in FIG. 32C, the position of the detector 110 is moved till the width of the inspection image 60 detected by the detector 110 is minimum.

Then, the user identifies, as Z1, the position in the Z direction of the detector 110 when the width of the inspection image 60 becomes minimum (step S158). Then, the user identifies the width in the X direction when the inspection image 60 is minimum (step S160). That is, as illustrated in FIG. 32C, the width Hi(Z1) in the X direction of the inspection image 60 is identified.

Then, the user calculates the size of the region of convergence with use of the values identified at step S154, S158, and step S160 (step S162). That is, the size of the region of convergence in the X direction is calculated from the difference (ID−Hi(Z1)) between the width Hi(Z1) in the X direction when the inspection image 60 is minimum and the dimension ID of the pupil 94. The size of the region of convergence in the Y direction is calculated from two times of the distance from the position Z0 in the Z direction of the detector 110 when the width of the inspection image 60 is equal to the width of the pupil 94 to the position Z1 in the Z direction of the detector 110 when the width of the inspection image 60 is minimum, i.e., (2(Z1−Z0)).

The eighth embodiment describes a case where the region of convergence of the scanning light is inspected by the user as an example, but the region of convergence of the scanning light may be inspected by the control unit of the inspection device (the control unit 18 in FIG. 1).

Although the embodiments of the present invention has been described in detail, the present invention is not limited to a certain embodiment, and it should be understood that the various change, substitutions, and alterations could be made hereto without departing from the scope of the invention.

DESCRIPTION OF REFERENCE NUMERALS 10 mounting unit
12 through 12b condensing lens
14, 14a target projection unit
16 imaging unit
18 control unit
20 image transformation unit
22 inspection unit
24 display unit
30 image projection device
50 light beam
52 dummy eye
54 convergence point
58 center point
60 inspection image
70 apertured plate
80 half mirror
82 polarizer
84 polarization beam splitter
86 quarter wavelength plate
100 through 700 image inspection device
110 Detector

The invention claimed is:

1. An image projection device comprising:
   a mounter on which an image projection device that directly projects an image on a retina of a user is to be mounted;
   a condensing lens configured to condense a light beam emitted from the image projection device mounted on the mounter;
   a detector on which an inspection image is to be projected by irradiation with the light beam condensed by the condensing lens and is configured to detect the inspection image; and
   a controller configured to inspect the inspection image detected by the detector,
   wherein
   the detector is movable in a direction vertical to a plane of the detector, and
   the controller is configured to measure a size of a region of convergence of the light beam by identifying a position of the detector and a size of the inspection image at the position as the detector moves.

2. The image inspection device according to claim 1, wherein
   the detector has a planar shape.

3. An image inspection method comprising:
   projecting an inspection image on a detector by causing a light beam forming the inspection image to be emitted from an image projection device that directly projects an image on a retina of a user, causing the light beam to pass through a condensing lens, and irradiating the detector with the light beam;
   detecting the inspection image by the detector:
   inspecting the inspection image detected by the detector;
   identifying a position of the detector, which detects an image, and a size of the inspection image detected at the position as the detector moves, the detector being movable in a direction vertical to a plane of the detector; and
   measuring a size of a region of convergence of the light beam by an identified position of the detector and an identified size of the inspection image.

4. The image inspection device according to claim 3, wherein
   the detector has a planar shape.

* * * * *